US009999513B2

(12) United States Patent
Overes et al.

(10) Patent No.: US 9,999,513 B2
(45) Date of Patent: Jun. 19, 2018

(54) SHOULDER PROSTHESIS ASSEMBLY

(71) Applicant: 41Hemiverse AG, Bettlach (CH)

(72) Inventors: Tom Overes, Langendorf (CH); Robert Frigg, Bettlach (CH)

(73) Assignee: 41HEMIVERSE AG, Bettlach (CH)

( * ) Notice: Subject to any disclaimer, the term of this patent is extended or adjusted under 35 U.S.C. 154(b) by 0 days. days.

(21) Appl. No.: 15/029,234

(22) PCT Filed: Oct. 13, 2014

(86) PCT No.: PCT/CH2014/000149
§ 371 (c)(1),
(2) Date: Apr. 13, 2016

(87) PCT Pub. No.: WO2015/051476
PCT Pub. Date: Apr. 16, 2015

(65) Prior Publication Data
US 2016/0256288 A1    Sep. 8, 2016

(30) Foreign Application Priority Data
Oct. 13, 2013   (CH) ..................................... 1746/13

(51) Int. Cl.
*A61F 2/40*  (2006.01)
*A61F 2/32*  (2006.01)
(Continued)

(52) U.S. Cl.
CPC .............. *A61F 2/4014* (2013.01); *A61F 2/32* (2013.01); *A61F 2/34* (2013.01); *A61F 2/36* (2013.01); *A61F 2/40* (2013.01); *A61F 2/4081* (2013.01); *A61F 2002/30028* (2013.01); *A61F 2002/30225* (2013.01); *A61F 2002/30332* (2013.01);
(Continued)

(58) Field of Classification Search
CPC ...... A61F 2/40; A61F 2/32; A61F 2/34; A61F 2/36; A61F 2/4014; A61F 2002/4029; A61F 2002/4033; A61F 2002/4037; A61F 2002/404–2002/4055; A61F 2/4059; A61F 2002/2825–2002/2832;
(Continued)

(56) References Cited

U.S. PATENT DOCUMENTS 3,837,008 A   9/1974 Bahler et al.
3,869,730 A   3/1975 Skobel
(Continued)

FOREIGN PATENT DOCUMENTS

DE   102006041551 A1   11/2007
EP         1004283 A2    5/2000
(Continued)

*Primary Examiner* — Alvin Stewart
(74) *Attorney, Agent, or Firm* — Mu P.C.

(57) ABSTRACT

The present application concerns a shoulder prosthesis assembly. The shoulder prosthesis assembly comprises a humeral stem including a first articulating coupling means, a base portion of a substantially disc shaped geometry including a second articulating coupling means. Said first articulating coupling means and said second articulating coupling means connect the stem to the base portion. The ratio between the circumference of the disc shaped base portion and the peripheral thickness of the disc shaped base portion is at least 18:1.

14 Claims, 22 Drawing Sheets

(51) Int. Cl.
*A61F 2/34* (2006.01)
*A61F 2/30* (2006.01)
*A61F 2/36* (2006.01)

(52) U.S. Cl.
CPC ............ *A61F 2002/30364* (2013.01); *A61F 2002/30367* (2013.01); *A61F 2002/30616* (2013.01); *A61F 2002/30635* (2013.01); *A61F 2002/30662* (2013.01); *A61F 2002/30663* (2013.01); *A61F 2002/30932* (2013.01); *A61F 2002/30937* (2013.01); *A61F 2002/3617* (2013.01); *A61F 2002/4018* (2013.01); *A61F 2002/4022* (2013.01); *A61F 2002/4029* (2013.01); *A61F 2002/4085* (2013.01); *A61F 2002/4088* (2013.01); *A61F 2002/4096* (2013.01); *A61F 2230/0093* (2013.01); *A61F 2230/0095* (2013.01)

(58) Field of Classification Search
CPC .................. A61F 2002/30378; A61F 2002/30649–2002/30652
USPC ........... 623/19.11–19.14, 22.15, 22.4, 22.45, 623/22.46, 22.42, 23.4, 22.18
See application file for complete search history.

(56) References Cited

U.S. PATENT DOCUMENTS

| | | | | |
|---|---|---|---|---|
| 3,903,549 A * | 9/1975 | Deyerle | A61F 2/34 | 606/309 |
| 3,979,778 A | 9/1976 | Stroot | | |
| 4,003,096 A | 1/1977 | Frey | | |
| 4,040,130 A * | 8/1977 | Laure | A61F 2/4261 | 623/21.13 |
| 4,279,041 A * | 7/1981 | Buchholz | A61F 2/32 | 403/123 |
| 4,678,472 A * | 7/1987 | Noiles | A61F 2/32 | 623/23.4 |
| 4,950,299 A * | 8/1990 | Noiles | A61F 2/32 | 623/22.18 |
| 4,957,510 A * | 9/1990 | Cremascoli | A61F 2/3662 | 623/22.46 |
| 4,960,427 A * | 10/1990 | Noiles | A61F 2/32 | 623/22.18 |
| 5,171,285 A * | 12/1992 | Broderick | A61F 2/34 | 623/22.25 |
| 5,314,485 A * | 5/1994 | Judet | A61F 2/4261 | 623/21.13 |
| 5,702,457 A * | 12/1997 | Walch | A61F 2/4014 | 623/19.13 |
| 5,888,207 A * | 3/1999 | Nieder | A61F 2/32 | 623/23.15 |
| 5,910,171 A * | 6/1999 | Kummer | A61F 2/4014 | 623/18.11 |
| 6,042,611 A * | 3/2000 | Noiles | A61F 2/34 | 623/22.21 |
| 6,083,263 A * | 7/2000 | Draenert | A61F 2/3609 | 623/22.46 |
| 6,197,062 B1 * | 3/2001 | Fenlin | A61F 2/4014 | 623/19.12 |
| 6,197,063 B1 * | 3/2001 | Dews | A61F 2/4014 | 623/19.14 |
| 6,676,705 B1 * | 1/2004 | Wolf | A61F 2/4014 | 623/19.14 |
| 6,719,799 B1 * | 4/2004 | Kropf | A61F 2/4014 | 623/19.12 |
| 6,749,637 B1 * | 6/2004 | Bahler | A61F 2/4014 | 623/19.11 |
| 7,011,686 B2 * | 3/2006 | Ball | A61F 2/4014 | 623/19.14 |
| 7,097,663 B1 * | 8/2006 | Nicol | A61F 2/4014 | 623/19.12 |
| 7,108,720 B2 * | 9/2006 | Hanes | A61F 2/32 | 623/22.11 |
| 7,135,044 B2 * | 11/2006 | Bassik | A61F 2/36 | 623/22.42 |
| 7,238,207 B2 * | 7/2007 | Blatter | A61F 2/4014 | 623/19.14 |
| 7,335,231 B2 * | 2/2008 | McLean | A61F 2/32 | 623/22.15 |
| 7,455,694 B2 * | 11/2008 | Epaules | A61F 2/32 | 623/22.15 |
| 7,615,080 B2 * | 11/2009 | Ondrla | A61F 2/4014 | 623/19.11 |
| 7,776,098 B2 * | 8/2010 | Murphy | A61F 2/3609 | 623/22.42 |
| 8,002,838 B2 * | 8/2011 | Klotz | A61F 2/4014 | 623/19.14 |
| 8,062,376 B2 * | 11/2011 | Shultz | A61F 2/40 | 623/19.11 |
| 8,123,814 B2 * | 2/2012 | Meridew | A61F 2/30724 | 623/22.19 |
| 8,357,204 B2 * | 1/2013 | Ragbir | A61F 2/3609 | 623/23.15 |
| 8,398,718 B2 * | 3/2013 | Richardson | A61F 2/34 | 623/22.11 |
| 8,454,702 B2 * | 6/2013 | Smits | A61F 2/40 | 623/19.11 |
| 8,663,333 B2 * | 3/2014 | Metcalfe | A61F 2/4014 | 623/19.11 |
| 8,906,102 B2 * | 12/2014 | Viscardi | A61F 2/4014 | 623/19.11 |
| 2002/0143402 A1 | 10/2002 | Steinberg | | |
| 2003/0074079 A1 * | 4/2003 | McTighe | A61F 2/30767 | 623/22.42 |
| 2003/0171817 A1 * | 9/2003 | Rambert | A61F 2/32 | 623/22.17 |
| 2003/0233146 A1 | 12/2003 | Grinberg et al. | | |
| 2004/0143335 A1 * | 7/2004 | Dews | A61F 2/4014 | 623/19.14 |
| 2005/0203634 A1 * | 9/2005 | Bassik | A61F 2/36 | 623/22.42 |
| 2005/0228502 A1 * | 10/2005 | Deloge | A61F 2/32 | 623/22.18 |
| 2006/0079963 A1 | 4/2006 | Hansen | | |
| 2006/0259148 A1 * | 11/2006 | Bar-Ziv | A61F 2/30767 | 623/19.14 |
| 2007/0043448 A1 * | 2/2007 | Murray | A61F 2/30767 | 623/22.46 |
| 2007/0112430 A1 * | 5/2007 | Simmen | A61F 2/40 | 623/19.14 |
| 2007/0173945 A1 * | 7/2007 | Wiley | A61F 2/30734 | 623/19.13 |
| 2008/0091274 A1 * | 4/2008 | Murphy | A61F 2/3609 | 623/22.42 |
| 2008/0140210 A1 * | 6/2008 | Doubler | A61F 2/4059 | 623/19.14 |
| 2008/0140211 A1 | 6/2008 | Doubler et al. | | |
| 2008/0281430 A1 * | 11/2008 | Kelman | A61F 2/30734 | 623/23.23 |
| 2009/0062923 A1 | 3/2009 | Swanson | | |
| 2009/0192621 A1 | 7/2009 | Winslow et al. | | |
| 2009/0281630 A1 * | 11/2009 | Delince | A61F 2/40 | 623/19.13 |
| 2010/0100193 A1 * | 4/2010 | White | A61F 2/46 | 623/22.43 |
| 2010/0211178 A1 * | 8/2010 | Nogarin | A61F 2/40 | 623/19.14 |
| 2010/0241239 A1 * | 9/2010 | Smith | A61B 17/1668 | 623/22.42 |
| 2011/0009976 A1 * | 1/2011 | Cruchet | A61B 17/1668 | 623/22.46 |
| 2011/0035021 A1 * | 2/2011 | Bergin | A61F 2/30734 | 623/22.42 |
| 2012/0004733 A1 * | 1/2012 | Hodorek | A61F 2/40 | 623/19.11 |
| 2012/0172992 A1 * | 7/2012 | Fockens | A61F 2/4059 | 623/19.13 |

(56) References Cited

U.S. PATENT DOCUMENTS

| | | | |
|---|---|---|---|
| 2012/0179262 A1* | 7/2012 | Metcalfe | A61F 2/4014 623/19.14 |
| 2013/0066433 A1* | 3/2013 | Veronesi | A61F 2/4081 623/19.13 |
| 2014/0107791 A1* | 4/2014 | Isch | A61F 2/4014 623/19.14 |
| 2014/0236304 A1* | 8/2014 | Hodorek | A61B 17/1778 623/19.14 |
| 2015/0039096 A1* | 2/2015 | McTighe | A61F 2/30767 623/23.35 |
| 2016/0113645 A1* | 4/2016 | Hardy | A61B 17/0401 623/19.14 |
| 2016/0166393 A1* | 6/2016 | Visser | A61B 17/68 623/19.14 |
| 2016/0193049 A1* | 7/2016 | McTigue | A61F 2/30767 623/19.14 |
| 2016/0235539 A1* | 8/2016 | Overes | A61F 2/40 |

FOREIGN PATENT DOCUMENTS

| | | |
|---|---|---|
| EP | 1314407 A1 | 5/2003 |
| FR | 2314702 A1 | 1/1977 |
| WO | 0176511 A1 | 10/2001 |
| WO | 2008000928 A2 | 1/2008 |
| WO | 2008026135 A1 | 3/2008 |
| WO | 2010105073 A1 | 9/2010 |
| WO | 2011006852 A1 | 1/2011 |

\* cited by examiner

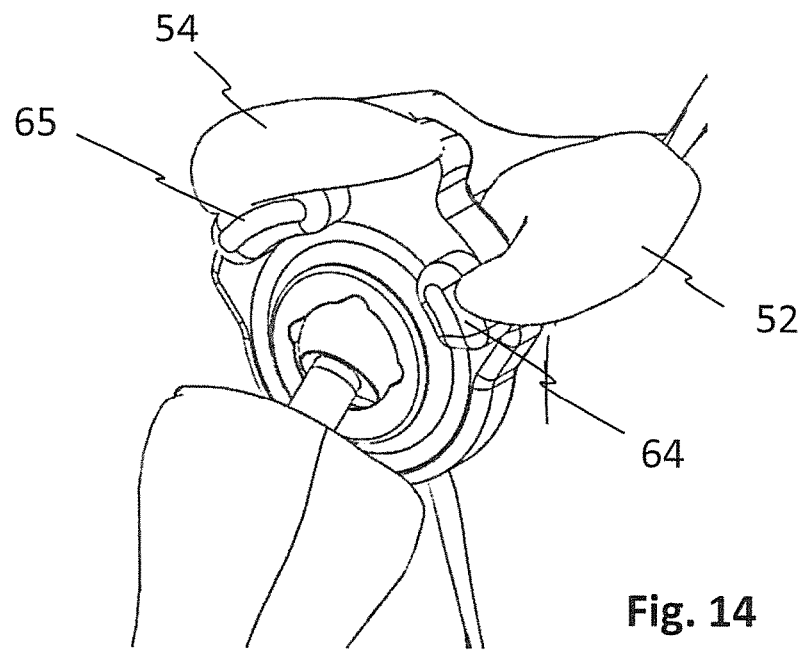
Fig. 14
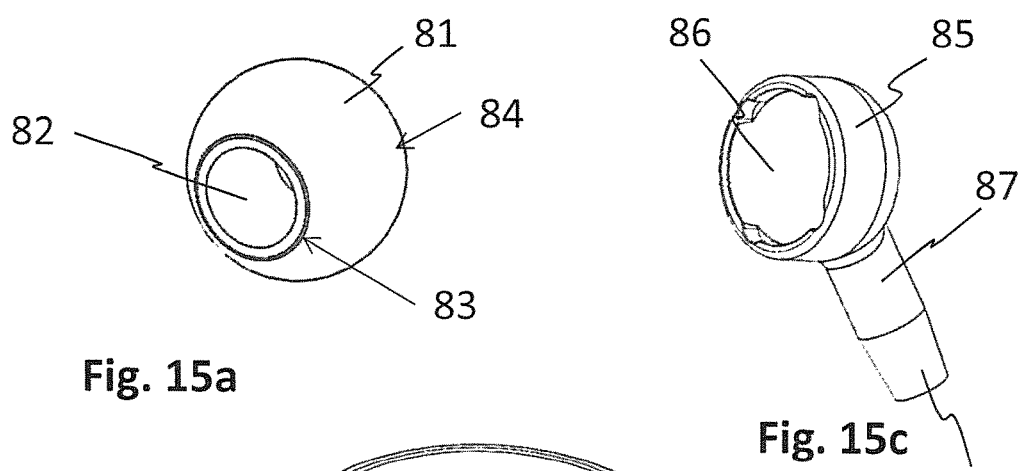
Fig. 15a
Fig. 15c
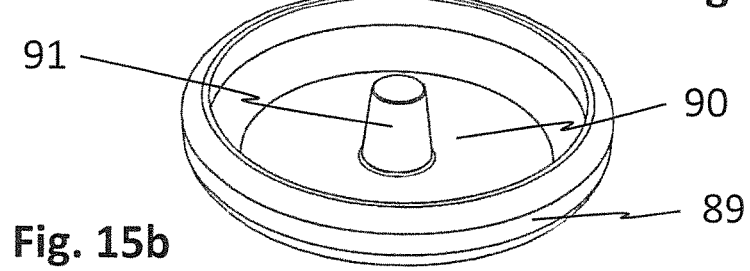
Fig. 15b

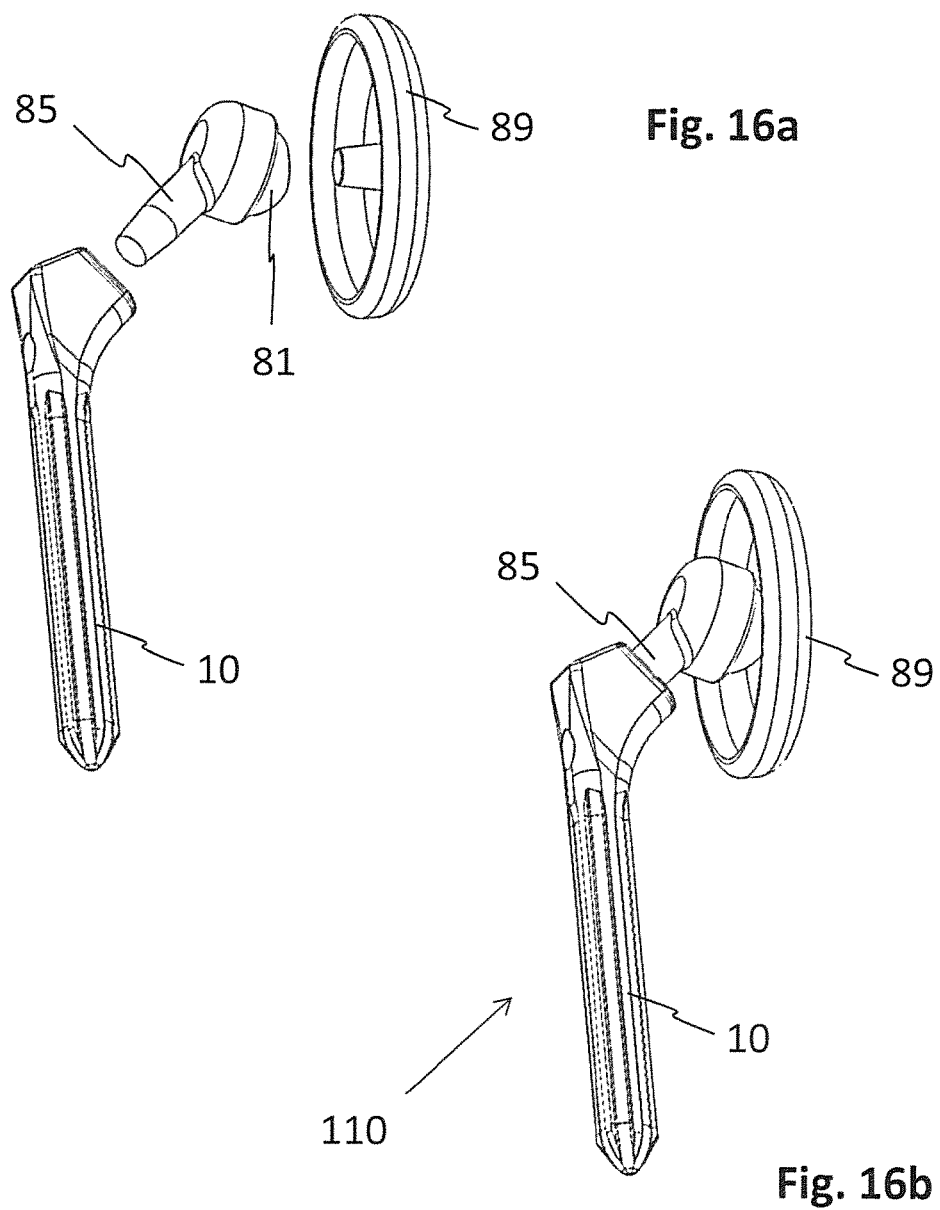

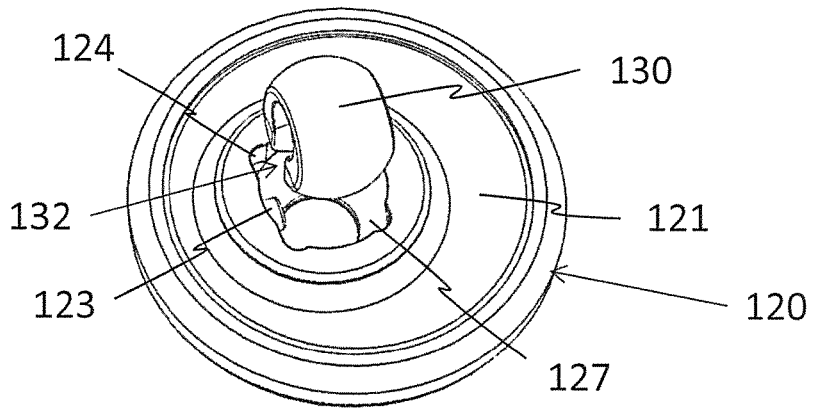
Fig. 19a
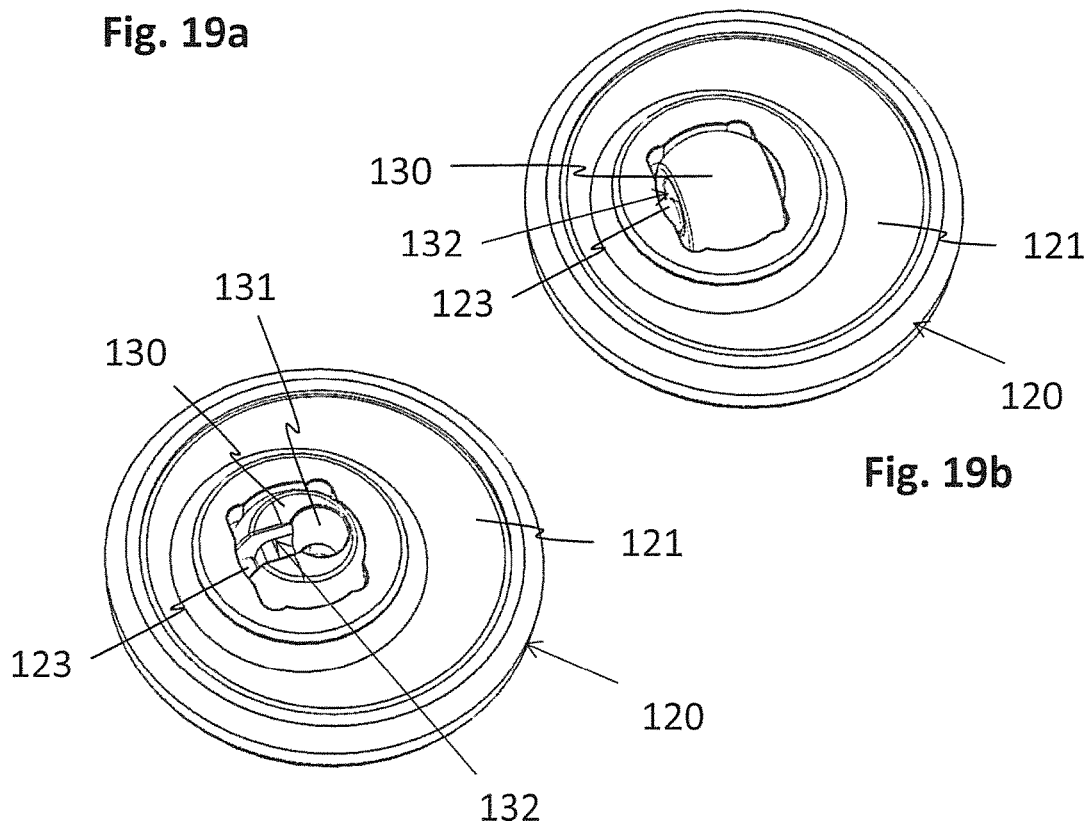
Fig. 19b
Fig. 19c

SHOULDER PROSTHESIS ASSEMBLY

TECHNICAL FIELD

The invention relates to surgical devices for performing shoulder arthroplasty.

BACKGROUND ART

The human shoulder consists of three bones: the clavicle/collarbone, the scapula/shoulder blade, and the humerus/upper arm bone, and furthermore includes multiple muscles, ligaments and tendons forming the rotator cuff. The articulations between the bones of the shoulder make up the shoulder joints. "Shoulder joint" typically refers to the glenohumeral joint, which is the joint where the humeral head articulates in the glenoid fossa.

The area of articulation has white cartilage on the ends of the bones, the so-called articular cartilage, which facilitates low friction movement or articulation between the bones. The shoulder must be mobile enough for the wide range motions of the arms and hands, but also stable enough to allow for motion such as lifting, pushing and pulling. This combination of stability and mobility results in large muscle reaction forces to the joint articulation surfaces Due to long term excessive loading, arthritis or trauma injury the cartilage may start to wear out which causes pain and stiffness. Due to rotator-cuff deficiency the joint may also lose its stability and therefore its functionality.

Shoulder replacement surgery is an option for treatment of unstable, non-functional and painful shoulder joints. The joint replacement surgery aims to relieve arthritic pain and to re-establish the functionality of the shoulder joint for daily activities. In a shoulder replacement surgical procedure the glenohumeral joint is partly or fully replaced by a prosthetic implant.

There are four common methods for shoulder replacement known in the art, namely: total shoulder replacement, reverse shoulder replacement, replacement with a hemi-prosthesis and replacement with a bi-polar prosthesis.

Total shoulder replacement involves the replacement of the ball and socket joint. An artificial head replaces the humeral head and a PE glenoid socket-like component replaces the cartilage on the glenoid cavity. Total shoulder replacement functions well in cases where the shoulder muscles, ligaments and tendons comprising the rotator-cuff show good functionality.

In cases where the rotator cuff is less functional a reverse prosthesis is used. The reverse prosthesis features a metal head or ball section that replaces the glenoid. The articulating socket is being implanted in the humerus. The method of reversing the socket and the head distalizes the humerus and medializes the centre of rotation, and herewith allows the deltoid muscle to compensate for the rotator cuff deficiency. Good functionality is reached with this method.

The hemi-prosthesis only replaces one half of the joint with an artificial surface. The humerus head is resected and replaced by a metal component. This metal component articulates against the natural glenoid.

More recently a bi-polar prosthesis has been introduced used in shoulder arthroplasty. A bi-polar prosthesis comprises a hemispherical humeral head, directly engaging with the glenoid, and a second ball-in-socket connection between the humeral head and the humeral shaft.

Both the bi-polar and a hemi-prosthesis are used to treat rotator cuff arthropathy of the shoulder in patients with low functional demands.

Different prosthesis for shoulder replacement are known in the art. For example, US 2006/0079963 A1 (Hansen Regan) discloses a shoulder replacement device for treatment of rotator cuff arthroplasty which comprises a glenoid component and a humeral component. The glenoid component is generally concave or cup-shaped and comprises structures for attaching the component to at least two, preferably three of the most lateral projections of the scapula, namely the acromion process, the coracoid process and the glenoid fossa. The glenoid component comprises two members which may be drilled into the bone. At a third location, the glenoid component may be anchored to the bone by means of bone cement. The humeral component comprises a generally spherical or hemispherical member which is anchored by a stem system into the humerus.

US 2009/062923 A1 (Swanson Todd) describes a method and apparatus for total shoulder arthroplasty. A glenoid component comprises a body having an outer surface configured to anchor to the scapula and to be located adjacent the clavicle and the acromion. The outer surface comprises at least one portion of tissue in-growing material, especially located in the area of contact to the scapula. In a first step, the glenoid component may be transiently anchored to the scapula by means of screws, pegs, bolts, wires or the like prior to the permanent anchoring accomplished by tissue and bone ingrowth.

EP 1 314 407 A1 (Sulzer Orthopedics Ltd.) discloses a shoulder prosthesis having a glenoid element with a cup-like bearing. The glenoid element is fixated to a bone of the shoulder by means of pegs which are secured in the bone with bone cement.

US 2009/0192621 A1 (Biomet Manufacturing Corp.) discloses an implant assembly for a shoulder joint which includes a planar base and a humeral stem. The implant assembly further comprises an adaptor to be arranged between said planar base and said humeral stem. The adaptor may comprise two different length axes such as to allow a displacement of the planar base and the humeral stem relative to each other.

SUMMARY OF THE INVENTION

It is the object of the invention to create a shoulder prosthesis pertaining to the technical field initially mentioned which has an increased stability and functionality.

The solution of the invention is specified by the features of claim 1.

Hence, the ball-and-socket coupling is rotationally arranged on the base portion via the inlay. The inlay is preferably provided in the form of a circular plate rotationally arranged on said base portion.

As one rotational degree of freedom of the ball-and-socket coupling is blocked, said coupling henceforth only includes two rotational degrees of freedom. However, the stem portion will retain three rotational degrees of freedom relative to the base portion, since the inlay has one rotational degree of freedom relative to the base portion.

Preferably, the proximal end of the base portion is configured to engage the surface of a glenoid cavity and the outer rim of the base portion is configured to engage with a coracoid process and an acromion process.

As used throughout the present application, the terms "proximal" and "distal" are used to describe the position of a feature in relation to the main body. In relation to a limb, especially of the arm, these terms define the location of a feature in relation to the attachment point of the limb to the main body.

Further, the terms "medial" and "lateral" are used to define the position of a feature in relation to the mediolateral axis of the body. I.e. a feature which is "medial" is oriented towards the centre of the main body, while a feature which is "lateral" is oriented away of the main body.

By the co-operation of both said first and said second articulating coupling means, the humeral stem portion may be moved in at least one direction relative to said base portion.

The term "peripheral thickness" is understood to relate to the thickness in the area of the circumference of the base portion. Preferably, the thickness of the base portion is invariant over the entire surface area of the base portion. However, certain areas of the base portion may be provided with an increased or decreased thickness.

The term "disc shaped" relates to the overall appearance of the base portion having a relatively small thickness in relation to its circumference rather than to the shape of the base portion. However, preferably, the base portion has a rounded shape. Most preferably, the base portion is provided in a circular or oval shape.

Alternatively, an outer rim of the base portion is in the form of a polygon or is irregularly shaped. This allows providing a base portion which has a shape adapted for a better contact with anatomical features, such as the coracoid process or the acromion process. Additionally, a polygonal or irregular shape is secured more efficiently against any rotation in the glenoid cavity.

The ratio between the circumference of the disc shaped base portion and the peripheral thickness of the disc shaped base portion may be at least 18:1.

With a ratio of at least 18:1 between the circumference and the peripheral thickness the base portion is relatively thin compared to its footprint. By providing such a base portion, the centre of rotation of the co-operating articulating coupling means may be shifted medially and distally compared to the natural centre of rotation of the shoulder. As a result, the deltoid muscle has to be active throughout the full range of motion of the arm such as to compensate the deficiency of the infra-spinatus muscle caused by this shift of the centre of rotation. This results in an increased stability and functionality of the shoulder prosthesis.

The three degrees of freedom coupling may have three rotational degrees of freedom. I.e. the first articulating coupling means and the second articulating coupling means are configured such as to form a coupling having at least three degrees of freedom.

The term "degree of freedom" is understood in the following application as being an indication on the number of independent relative motions the coupling allows. For example, rotations around an axis of rotation or a linear movement along an axis both constitute separate degrees of freedom. A coupling allowing rotation around two separate axes of rotation would therefore comprise two degrees of freedom.

The coupling preferably has three rotational degrees of freedom, i.e. the coupling allows rotation of the stem portion relative to the base portion around three separate axes of rotation. More preferably, these three axes of rotation are all arranged orthogonal to each other.

Preferably, the base portion is movably coupled to the stem portion by means of a ball-and-socket connection. A ball-and-socket connection comprises a low number of parts and is hence easy and cheap to manufacture while offering a high level of reliability. Further, ball-and-socket connections allow a maximal freedom of movement.

Alternatively preferably, the base portion is movably coupled to the stem portion by means of a gimbal-mount coupling. A gimbal-mount coupling has the advantage that no dislodgment is possible as is the case with a ball-and-socket connection.

Preferably, said ball-and-socket coupling is arranged eccentrically in relation to the rotation axis of the inlay relative to the base portion. This allows a restricted motion of the stem portion relative to the base portion in two translational degrees of freedom.

Said second articulating coupling means of said ball-and-socket connection preferably comprises a spherical articulation cavity or a socket. Said spherical articulation cavity thereby includes a groove and said socket includes a channel, wherein said groove or said channel is oriented parallel or perpendicular to an imaginary line connecting the axis of rotation of said inlay and a rotational centre of said ball-and-socket coupling.

Provision of such an oriented groove or channel reduces the occurrence of torsional moments on the inlay when the humeral stem is subjected to forces.

Preferably, said ball-and-socket connection comprises a ball-head in the form of a spherical cap, a connection interface for connecting said humeral stem portion with said substantially spherical ball-head being arranged on the base of said spherical cap, wherein said connection interface is located offset of the centre of the base of the spherical cap.

In the present application, a "spherical cap" is understood to constitute a portion of sphere cut off by a plane. The sectional plane is referred to as "base" of the spherical cap.

Provision of the coupling interface at a location which is eccentric with the centre of the base allows imparting some limited linear motion of said coupling interface, and hence of a humeral stem portion coupled therewith, in two linear degrees of motion relative to the base portion.

Preferably, said connection interface is in the form of a female taper, into which a corresponding male taper of the humeral stem portion may be inserted.

Preferably, said ball-head is provided in the form of a spherical segment and a socket of said ball-and-socket coupling has an opening which is smaller than a largest diameter of said spherical segment but larger than a distance between bases of said spherical segment.

As used in the present application, "a spherical segment" is a sphere cut by two substantially parallel planes. Such a spherical segment comprises two sectional planes which are both referred to as bases. More preferably, the cutting planes are both spaced from the centre of the ball-head by an equal distance, i.e. the bases of the spherical segment are arranged symmetrically relative to the centre of the ball-head.

Provision of the ball-head as spherical segment allows locking the ball-head in the socket while retaining the possibility of inserting or removing the ball-head into or from said socket. Specifically, said ball-head may be inserted into said socket in a first orientation where the bases are at a right angle to said opening. By turning the ball-head by 90° such that one of the bases is oriented parallel to the opening, the ball-head is securely locked within said socket.

Preferably, the base portion is dimensioned such that a distance between the centre of rotation of said coupling and a base area of said base portion is less than 15 mm.

In the present application, the term "base area" is used to denominate the surface of the base portion which is intended to engage the surface of the glenoid cavity and to contact the coracoid process and the acromion process with its rim. Hence, the base area is located facing away of the second coupling means.

By providing such a "flat" base portion allows to further medialize and distalize the centre of rotation of the inventive shoulder prosthesis in comparison to prosthesis as known in the art. This further helps activating the deltoid muscle throughout the full range of motion which compensates for deficiency of the infra-spinatus muscle.

Preferably, said shoulder prosthesis further includes a substantially Z-shaped adaptor arranged between said ball-head and said humeral stem portion.

By means of said adaptor, the humeral bone may be arranged further laterally and distally in relation to the centre of rotation of the coupling. Further, a surgeon may adapt the shoulder prosthesis individually to a patient by selecting an appropriate adaptor.

Preferably, the adaptor comprises two taper connections, wherein the central axes of the taper connections are oriented either offset in one direction and parallel to each other or offset in one direction and under an acute angle to each other.

This allows providing different types of adaptors, such that for any given patient one adaptor may be selected which has a geometry which best suits the patient's anatomy. Hence, the shoulder prosthesis assembly according to the present invention may be adapted in a patient specific manner.

Preferably, at least one portion of a rim of said base portion comprises an increased thickness. Provision of areas with an increased thickness allow to provide a better stress distribution on the bone once the shoulder prosthesis assembly is implanted, as the contact surface to certain bones, such as the acromion and coracoid may be increased.

Preferably, the shoulder prosthesis comprises a base portion with a proximal face and an outer rim with a circumference, wherein the proximal face has a concave, convex or conical surface with a height or a depth, wherein the circumference to height ratio or circumference to depth ratio is at least 15:1, preferably larger than 20:1.

Other advantageous embodiments and combinations of features come out from the detailed description below and the totality of the claims.

BRIEF DESCRIPTION OF THE DRAWINGS

The drawings used to explain the embodiments show:

FIG. 14 an embodiment of a base portion with areas of increased thickness;

FIGS. 15a -15c components of another embodiment of a shoulder prosthesis assembly according to the present invention;

FIGS. 16a, 16b a shoulder prosthesis assembly using the components as shown in FIGS. 15a -15c;

FIGS. 19a -19f the interplay between the elements of the alternative ball-and-socket coupling according to FIGS. 18a, 18b;

In the figures, the same components are given the same reference symbols.

PREFERRED EMBODIMENTS

Figure 1A:
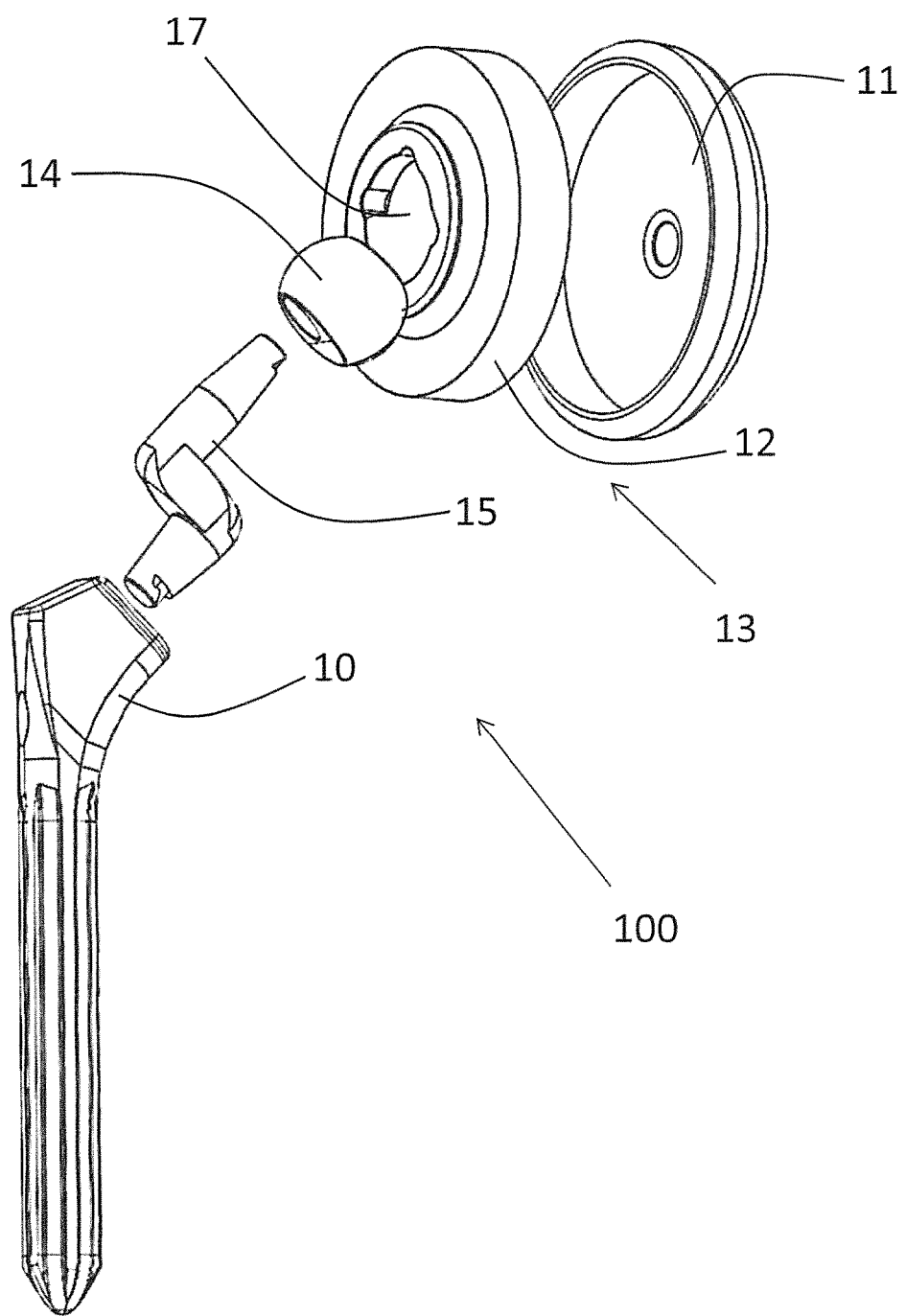
FIGS. 1a-1c A first embodiment of an inventive shoulder prosthesis assembly according to the present invention.
Figures 1B, 1C:
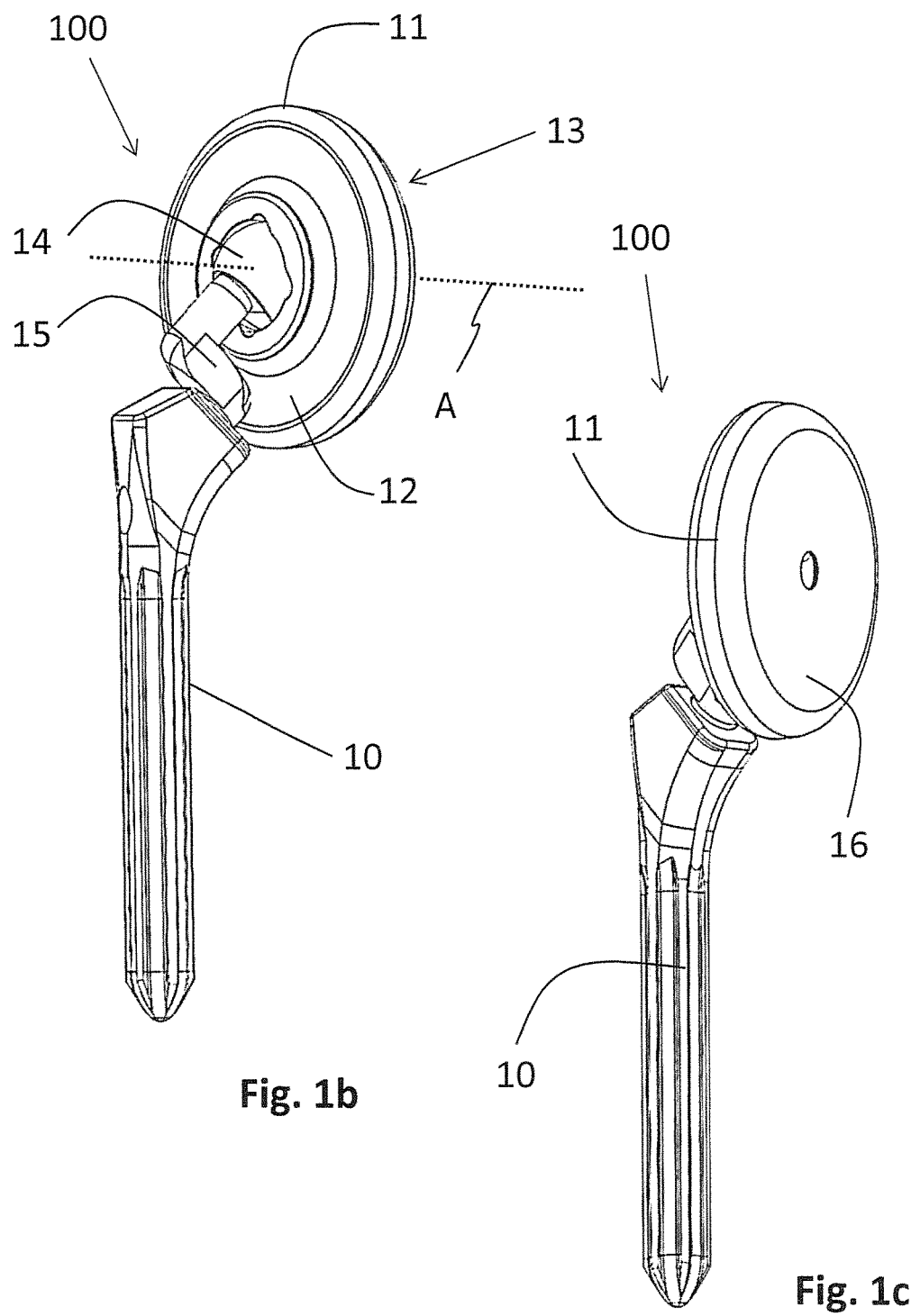

With reference to FIGS. 1a to 1c, an inventive shoulder prosthesis assembly 100 is shown. In FIG. 1a an exploded view shows the shoulder prosthesis assembly 100 comprising a humeral stem 10, a ball-head 14, an adaptor 15 and a disc shaped base portion 13, the so-called glenoid disc. Said base portion comprises an outer metal base 11 with an integrated articulation inlay 12. Said articulation inlay 12 is rotatable relative to said outer metal base 11.

FIGS. 1b and 1c show the assembled shoulder prosthesis assembly 100 from two different perspectives. The substantially spherical ball-head 14 is inserted into and articulates within a spherical cavity or socket 17 of the base portion 13. Said socket 17 is thereby located in said articulation inlay 12. The ball-head 14 and the socket 17 form a ball-and-socket connection which allows movement of the humeral stem portion 10 around three rotational degrees of freedom relative to the base portion 13.

In the embodiment shown, the base portion 13 is substantially circular with a central axis of rotation A. Said axis of rotation A coincides with the centre of the socket 17. The outer metal base 11 may comprise a polished or treated base area 16 to prevent from bone ingrowth. Said base area is intended to be arranged against the glenoid cavity.

In accordance of a variant of the invention, the prosthesis assembly 100 could consist of two monoblock components, namely the humeral stem 10 including the spherical ball-head 14 and the base portion 13 including socket 17. Such as to facilitate an adaptation of the spatial relationship of the individual elements of the prosthesis assembly 100 to the patient specific anatomy, or such as to convert a standard primary or reverse prosthesis into the described inventive prosthesis assembly 100, multiple parts may be provided, as the prosthesis assembly 100 is a modular construct of the elements humeral stem 10, adaptor 15, ball-head 14, articulation inlay 12 and outer metal base 11, as shown in figure 1a.

Figure 2A:
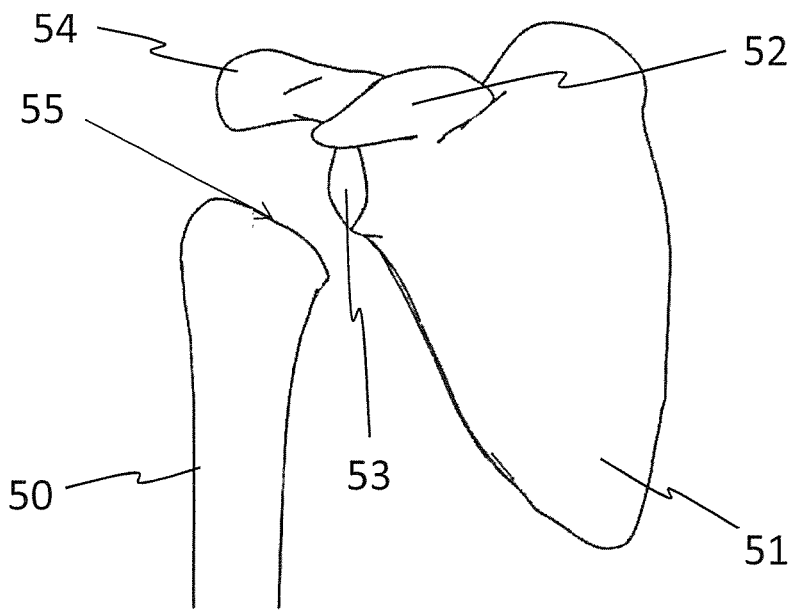
FIGS. 2a, 2b the relevant bone anatomy for positioning of a shoulder prosthesis assembly according to FIGS. 1a to 1c.
Figure 2B:
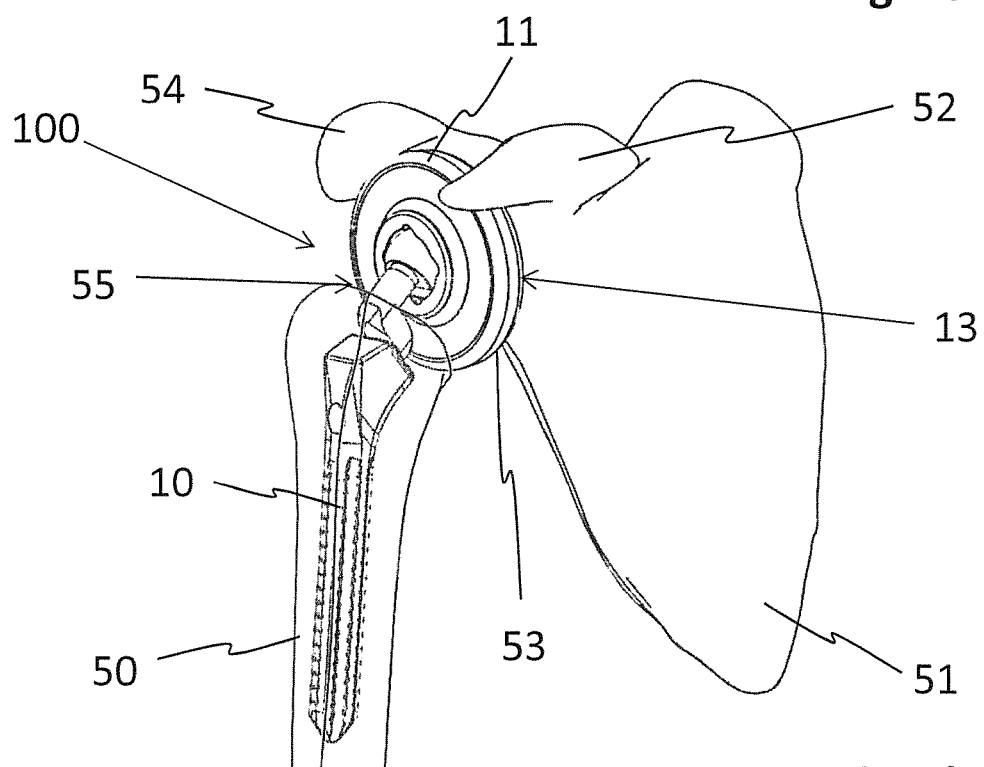

Referring to FIGS. 2a and 2b, the relevant bone anatomy for positioning of the shoulder prosthesis assembly 100 inside the humeral-scapular joint is shown. FIG. 2a shows the scapula 51 and the humerus 50, with resected humeral head 55. Parts of the bone of the scapula 51, namely the coracoid process 52, acromion process 54 and the glenoid 53 engage with the base portion 13 by means of the outer metal base 11, as shown in FIG. 2b, wherein the humeral stem portion 10 is fixated into the bone of the humerus 50. The base portion 13 is constrained by the coracoid process 52, the acromion process 54 and the glenoid 53, but not rigidly fixated, thus more or less floating within the joint capsule. The forces directed towards the cranial and medial sides of the rotator cuff, deltoid muscle and shoulder capsule pull the shoulder prosthesis assembly against the bony structures and keep it in place.

With reference to the description in relation to FIGS. 1a to 1c and 2a, 2b, the shape for the base portion 13 is circular. During movements of the arm for daily activities, rotational moments and forces may cause the non-fixated base portion to rotate over the glenoid 53. However, the constant distance of the centre of rotation of the socket 17 to the outer diameter of the base portion 13 guarantee a constant position of the centre of rotation of the ball-and socket connection.

Figure 3:
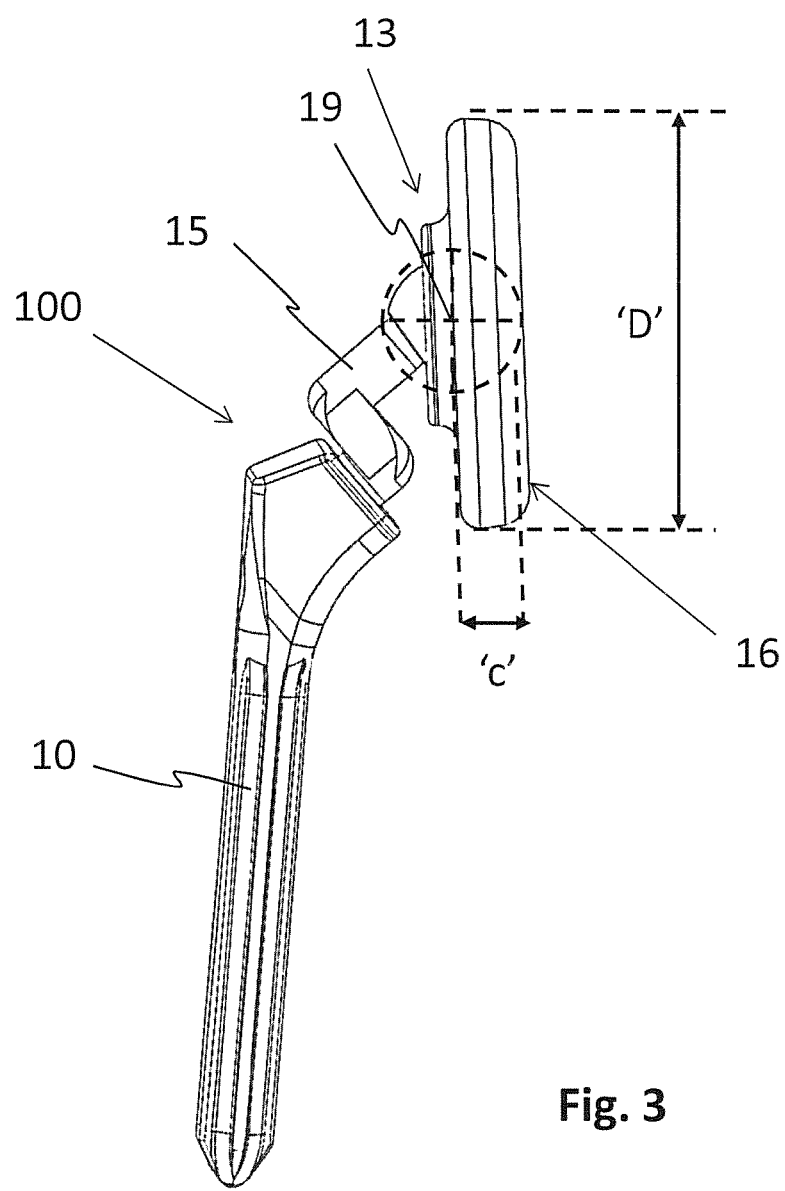
FIG. 3 a side view of the shoulder prosthesis assembly according to FIGS. 1a to 1c.

FIG. 3 shows a side view of the shoulder prosthesis assembly 100. In this figure, the centre of rotation 19 of the ball-and-socket connection between the ball head 14 and the socket 17 is shown. The ratio between the diameter D—and hence of the circumference—of the base portion 13 and the distance c of the centre of rotation 19 to the base area 16 results in a far distalised and medialised centre of rotation 19 in comparison to the natural shoulder. As a result, the deltoid muscle will be active throughout the full range of motion and compensate for deficiency of the infra-spinatus muscle.

Figure 4A:
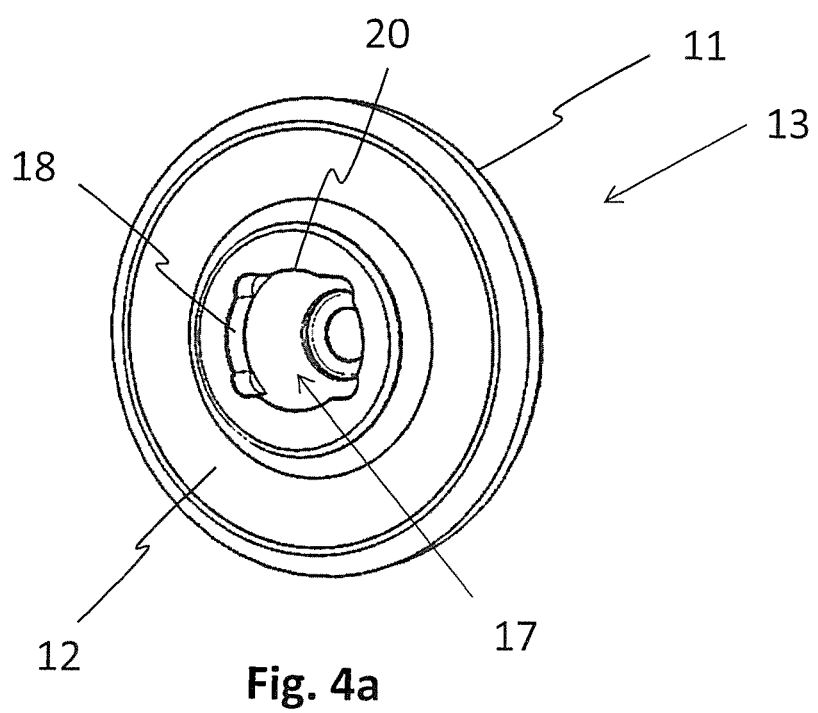
FIGS. 4a, 4b a perspective view and a side view of a base portion.
Figure 4B:
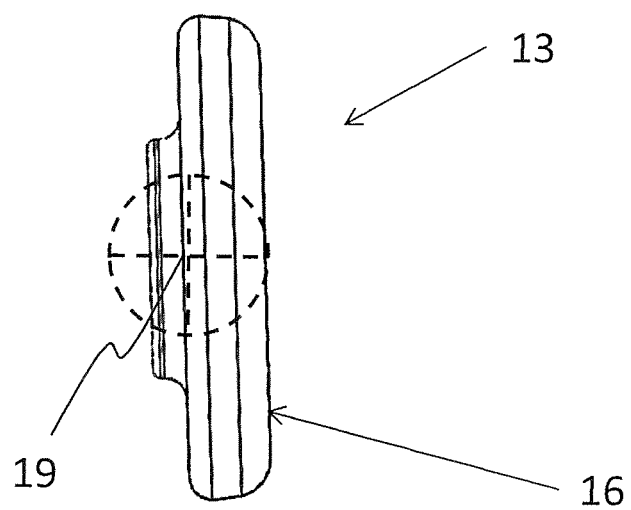

FIGS. 4a and 4b show a perspective view and a side view of the base portion 13. The base portion 13 comprises the outer metal base 11 as well as the articulation inlay 12. A spherical cavity forming the socket 17 is arranged centrally on said articulation inlay 12. In the embodiment as shown in FIG. 4b the rotation centre 19 of the ball-and-socket joint is arranged at a distance of approximately half the diameter of the socket 17 from the proximal end of the base portion 13. Further, the socket 17 intersects with a pocket 18. The pocket 18 is substantially perpendicular to the base portion 13 and has a depth which reaches to at least the largest circumference of the socket 17. Further, the width of the pocket 18 is significantly smaller than a border circumference 20 of the socket 17.

Figure 5:
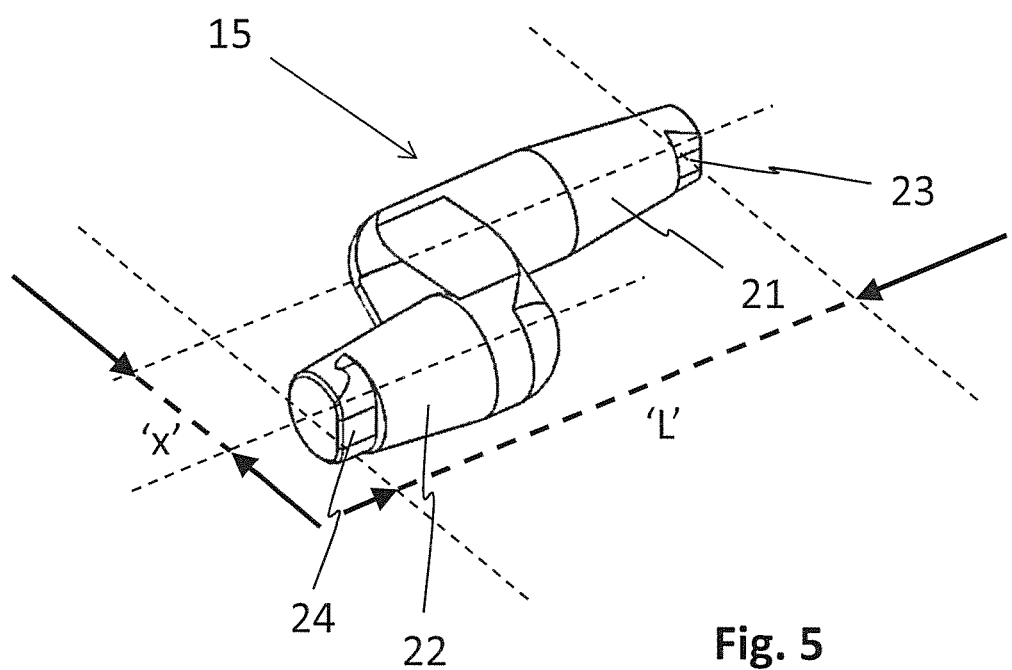
FIG. 5 a Z-shaped adaptor for an inventive shoulder prosthesis assembly according FIGS. 1a-1c.

FIG. 5 shows a Z-shaped adaptor 15 comprising a first tapered end 21 and a second tapered end 22 with substantially parallel axes. Both tapered ends 21, 22 comprise a recess 23, 24 at the end of the taper. The recesses 23, 24 serve as anti-rotation face as described in greater detail for the FIG. 7.

Figure 6A:
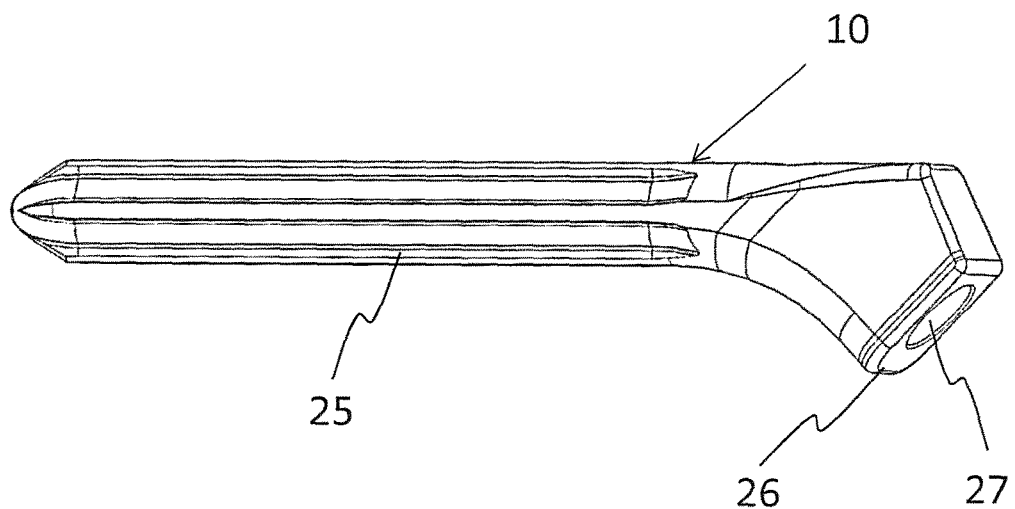
FIG. 6a, 6b a humeral stem for an inventive shoulder prosthesis assembly according to FIGS. 1a-1c.
Figure 6B:
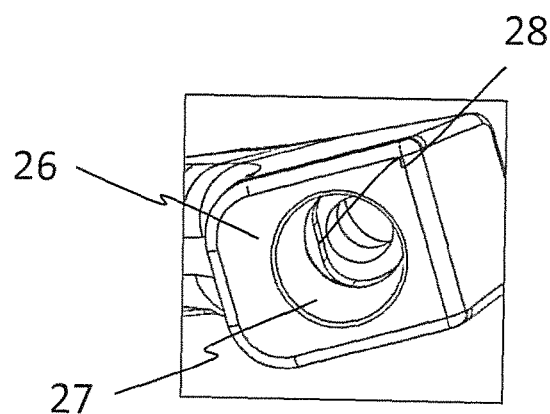

FIGS. 6a and 6b show the humeral stem 10. The humeral stem 10 comprises a shaft portion 25, a proximal end 26 and a female taper-connection 27 with an integrated antirotation protrusion 28 at the bottom of the female taper-connection 27.

Figure 7A:
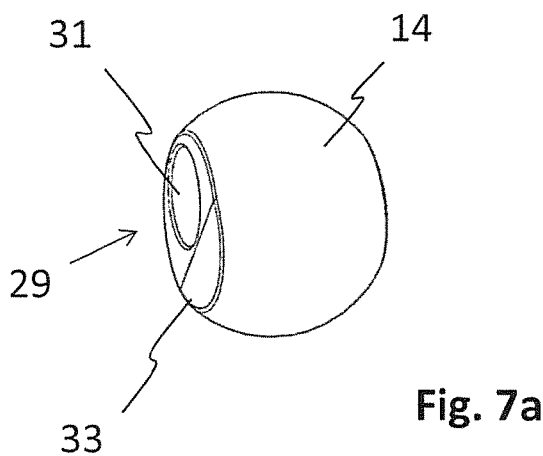
FIGS. 7a -7c a ball-head for an inventive shoulder prosthesis assembly according to FIGS. 1a-1c.
Figure 7B:
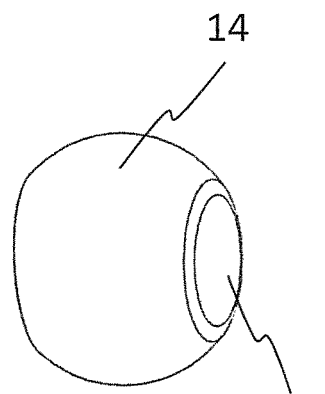
Figure 7C:
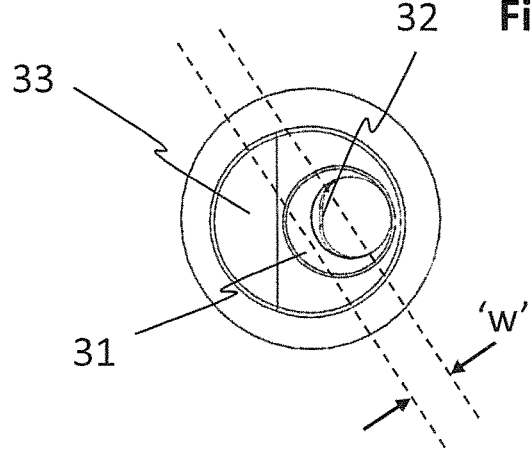

FIGS. 7a to 7c show the ball-head 14 comprising an outer geometry which is based on a full sphere with at least a first cut-off section 29, wherein the first cut-off section 29 is significantly smaller than a hemisphere, thus resulting in an overall shape of the ball-head as sphere with a face 33, or spherical cap. The ball-head comprises a second cut-off section 30, substantially aligned with the first cut-off section 29. The second cut-off section 29 is significantly smaller than a hemisphere. The resulting shape of the ball-head 14 is a disc with a spherical outer geometry, or spherical segment. The first cut-off section 29 comprises an attachment means 31 to be attached to the humeral stem 10 or with the adaptor 15. In the embodiment shown, the attachment means 31 is in the form of a female taper connection with an integrated anti-rotation protrusion 32 at the bottom of the taper connection. Further, the attachment means 31 is located eccentrically on the face 33 at a distance 'w' from the centre of said face 33, providing a larger range of motion for the ball-and-socket joint in defined directions, in comparison to other directions.

Figure 8A:
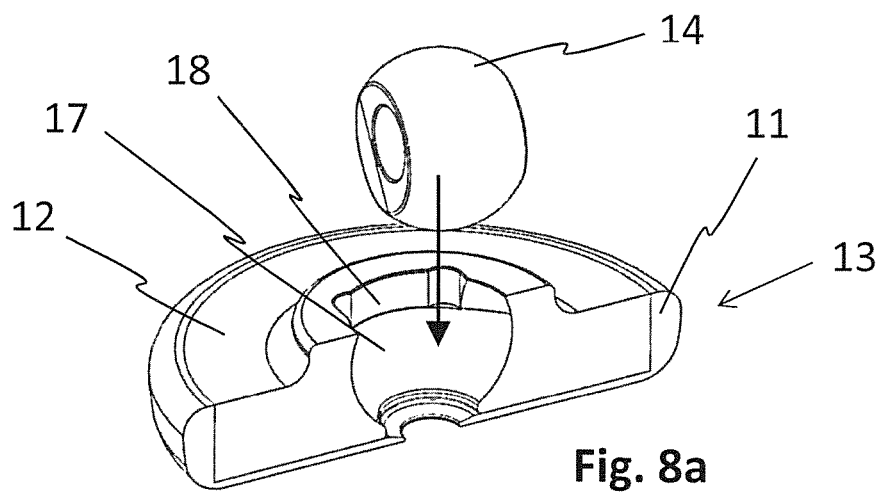
FIGS. 8a -8g assembly steps for an inventive shoulder prosthesis assembly according to FIGS. 1a-1c.
Figure 8B:
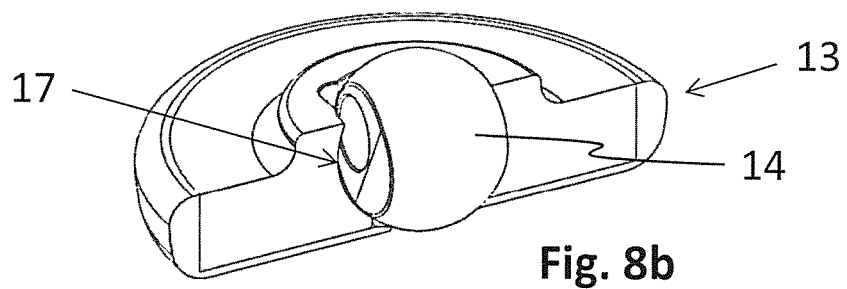
Figure 8C:
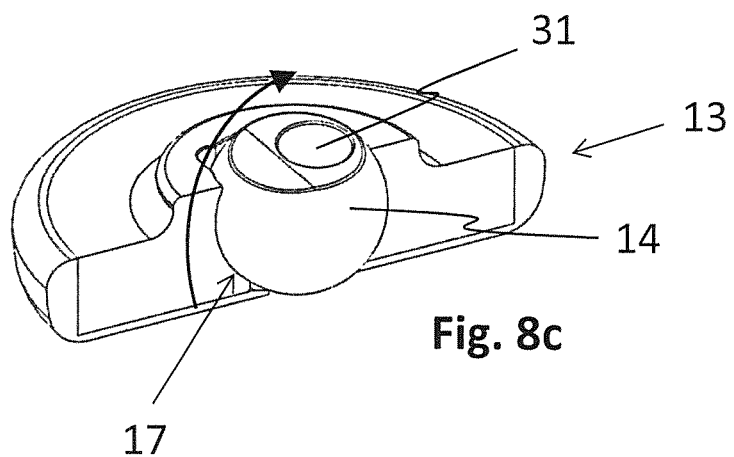

FIGS. 8a to 8g depict the assembly steps of the different components into a prosthesis assembly 100. In a first step, the articulation inlay 12 is snapped into the outer metal base 11, forming the base portion 13. In a second step, shown in FIG. 8a, the ball-head 14 is inserted into the socket 17 of the articulation inlay 12. The ball-head 14 is inserted by orienting both faces of the ball-head 14 perpendicular to the sidewalls of pocket 18. When a first end-position is reached, as shown in FIG. 8b, the ball-head 14 and the socket 17 are concentrically aligned. Then, the ball-head 14 is turned by 90° into a second end-position wherein the attachment means 31 are accessible through pocket 18, as shown in FIG. 8c.

Figure 8D:
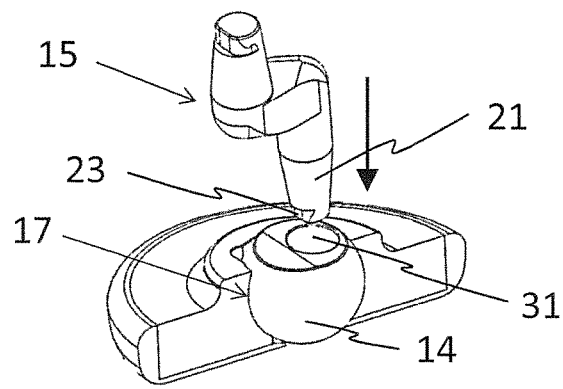
Figure 8E:
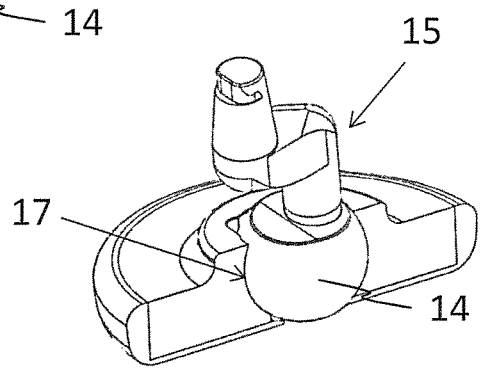

In a next step, shown in FIG. 8d, the adaptor 15 is placed into the attachment means 31 of the ball-head 14 with the first tapered end 21. Thereby, the recess 23 of the first tapered end 21 match with the anti-rotation protrusion 32 of the attachment means 31. Once the adaptor 15 is fully inserted into the attachment means 31, as shown in FIG. 8e, the ball-head 14 is prevented from rotating far enough to reach the assembly orientation as illustrated by FIGS. 6a and 6b. Therefore the ball-head 14 is locked within the socket 17 by a form fit connection.

Excessive movement of the arm which exceeds the range of motion of the shoulder prosthesis assembly 100 may cause the humeral stem 10 to impinge with the base portion 13. This will result in a momentum which in state of the art designs may cause a luxation of both implant components. The positive fit between the ball-head 14 and the socket 17 prevents the occurrence of such a luxation with a shoulder prosthesis assembly 100 according to the present invention.

Figure 8F:
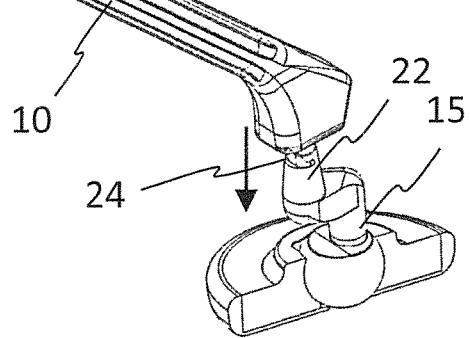

In a next step, shown in FIG. 8f, the humeral stem 10 is assembled with the second tapered end 22 of the adaptor 15. Thereby, the second recess 24 of the second tapered end 22 matches with the anti-rotation protrusion 28.

In matters of the anti-rotation faces, a taper connection is designed for transfer of rotational forces. The form-fit of the mating faces will resist any rotational moments around the axes of each taper connection.

Figure 8G:
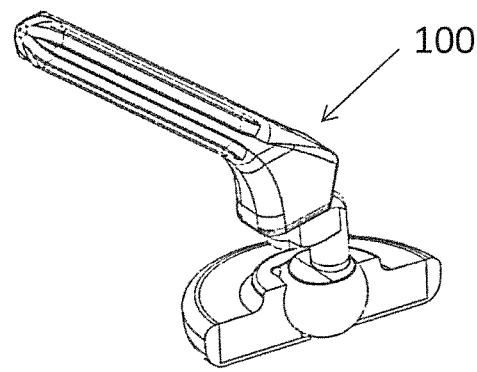

The final configuration of the shoulder prosthesis assembly 100 is shown in FIG. 8g.

Figure 9:
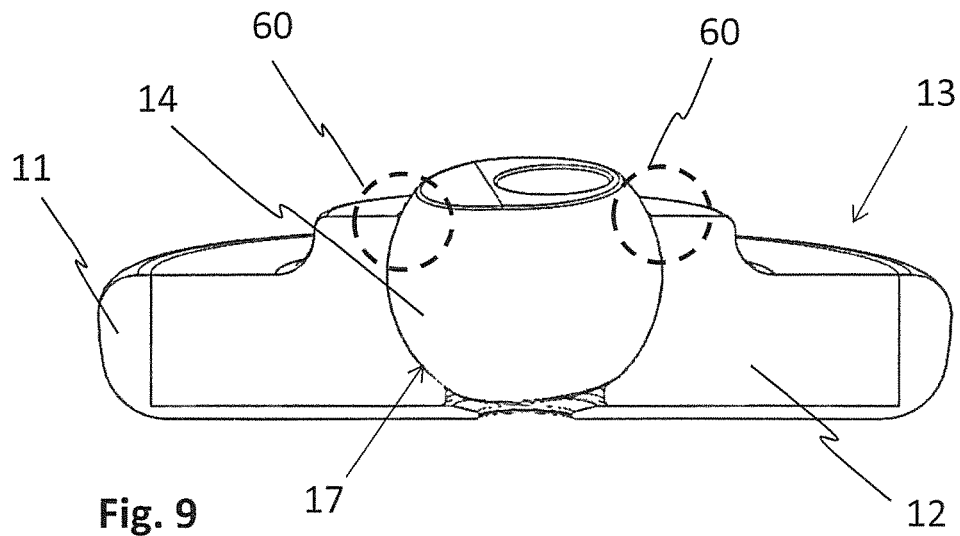
FIG. 9 a sectional cut of an assembly between a base portion and a ball-head.

FIG. 9 shows the assembly between the base portion 13 and the ball-head 14 as a sectional cut. As may be seen in this figure, the ball-head 14 is locked within the socket 7 in a form-fitting manner in the area 60 located beneath a rim of the socket 17.

Figure 10:
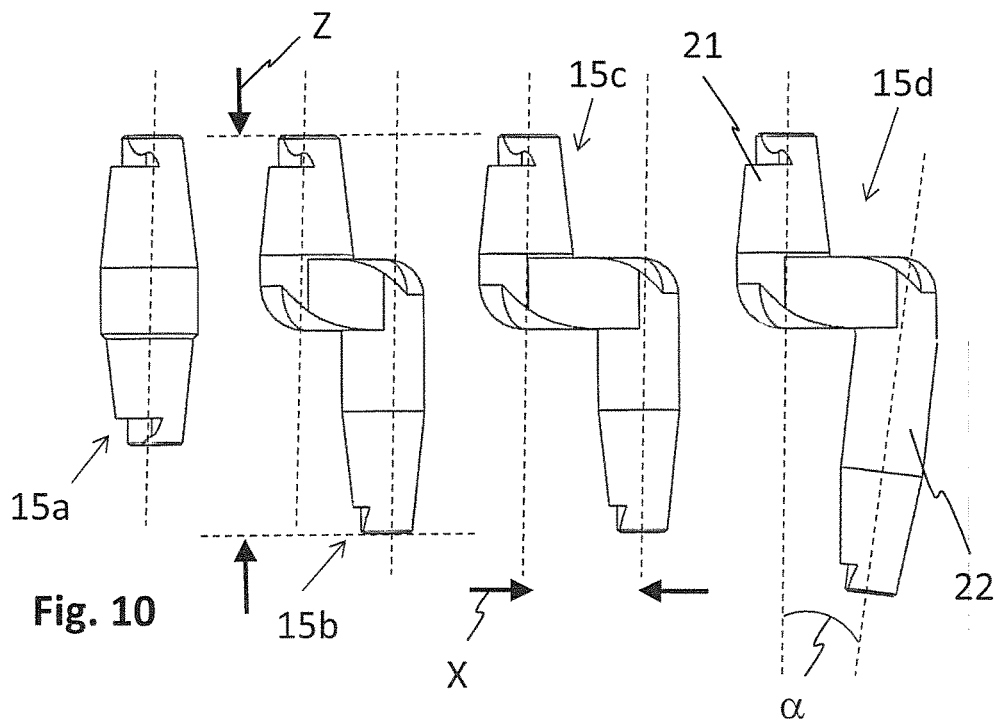
FIG. 10 different Z-shaped adaptors.

As shown in FIG. 10, different adaptors 15a-15d allow adapting the spatial relationship of the individual elements of the shoulder prosthesis assembly 100 to the specific patient anatomy. The distance X between the central axes of the first tapered end 21 and the second tapered end 22, the length L of the adaptor 15 as well as the angle a between the central axes of the first tapered end 21 and the second tapered end 22 may vary. By this variation, it is possible to individually distalize and lateralize the humeral bone and humeral stem 10 in relation to the centre of rotation 19 of ball-head 14.

Figure 11:
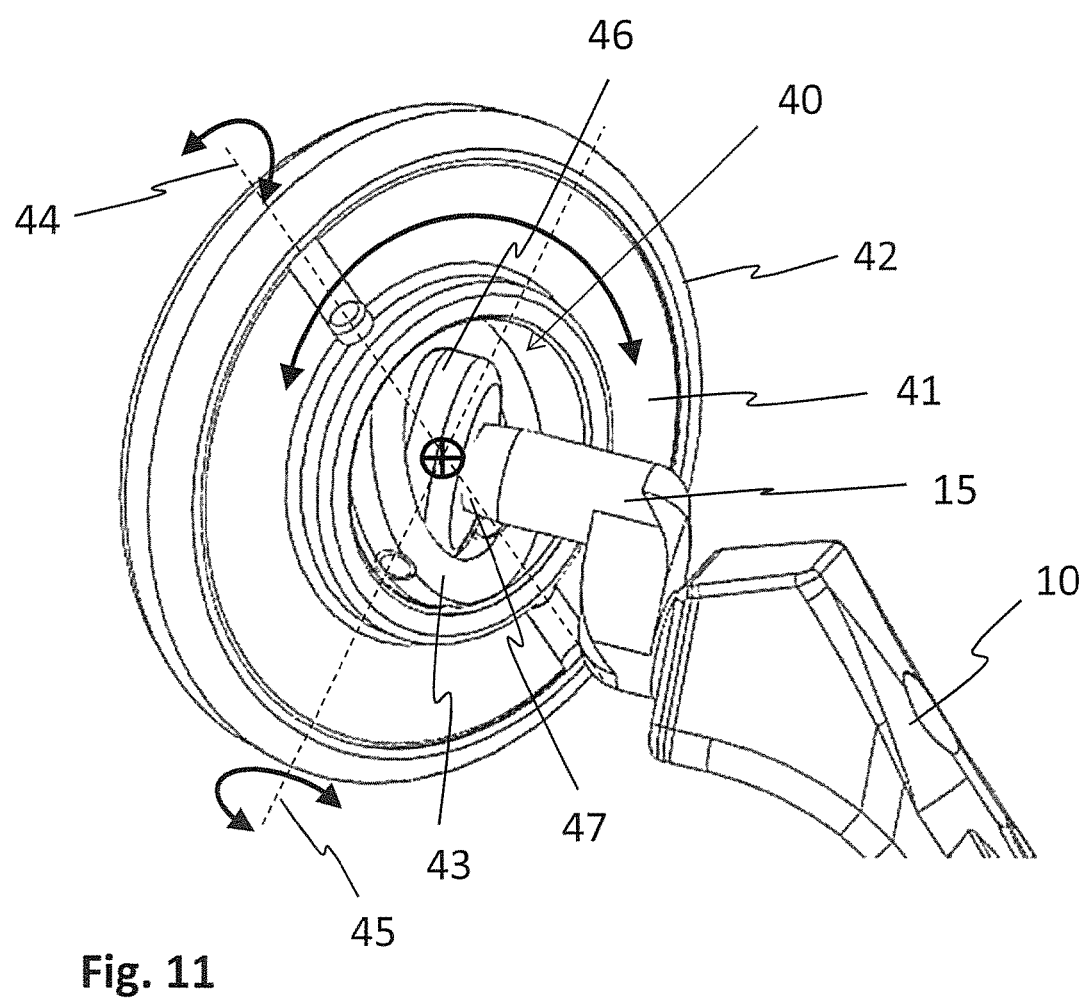
FIG. 11 a variant of the shoulder prosthesis assembly with an alternative coupling mechanism in the form of a gimbal-mount coupling.

FIG. 11 shows a variant of the present invention with an alternative coupling mechanism, namely a gimbal-mount coupling 40. The base portion 13 comprises a circular inner inlay 41 which is rotatably coupled to the outer metal base 42. Further, an inner ring 43 with a first axis of rotation 44 is rotatably coupled to the circular inner inlay 41. A centre portion 46 is rotatably coupled to the inner ring 43 via a second axis of rotation 45. The centre portion 46 furthermore comprises connection means 47 for connecting to the humeral stem 10 or to the adaptor 15.

The rotation axis of the inner inlay 41 is oriented substantially perpendicular to the outer metal base 42 and does not intersect the first axis of rotation 44 or the second axis of rotation 45. The eccentric position facilitates a further distalised centre of rotation without increasing the diameter of the glenoid disc.

Figure 12:
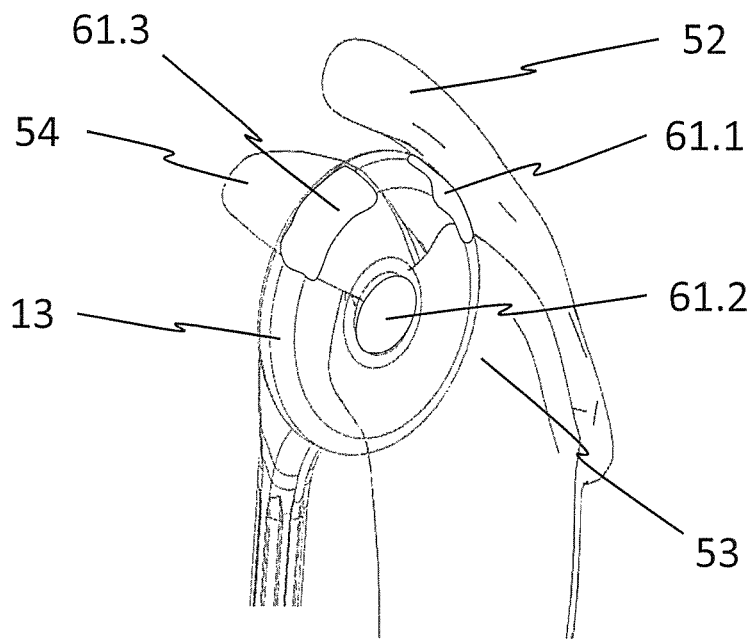
FIG. 12 a variant of the base portion having bone in growth areas.

FIG. 12 shows a variant of the base portion 13 comprising three bone in growth areas 61.1, 61.2, 61.3. The bone in growth areas 61.1, 61.2, 61.3 are located on the base portion 13 such as to engage with the glenoid 53, coracoid 52 and acromion 54.

Figure 13:
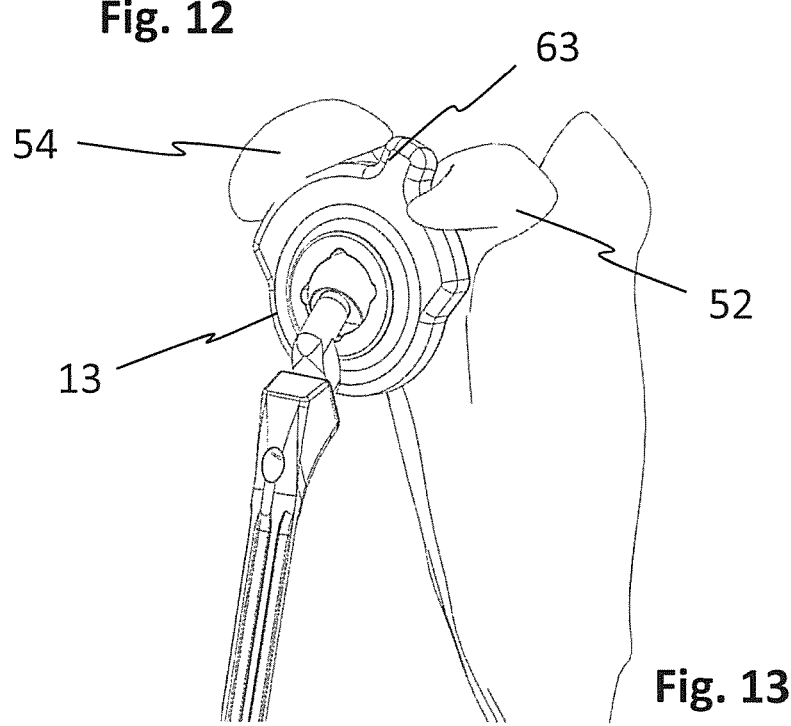
FIG. 13 a further embodiment of a base portion with an irregular shape.

FIG. 13 depicts a further embodiment of the base portion 13. In this embodiment, the base portion 13 is irregularly shaped and comprises a protrusion 63 which may be positioned between the coracoid 52 and the acromion 54. The protrusion 63 prevents rotation of the 10 base portion 13.

Another variant of the base portion 13 is shown in FIG. 14. The base portion 13 comprises two areas of increased thickness, namely a first engagement surface 64 engaging with the coracoid 52 and a second engagement surface 65 engaging with acromion 54. The two engagement surfaces 64, 65 allow for a better stress distribution on the bone.

FIGS. 15a to 15c show components of another embodiment of a shoulder prosthesis assembly 110 according to the present invention. In this embodiment, the ball-head 81 comprises a central taper connection 82 and two cut-off faces 83, 84, as shown in FIG. 15a. The base portion 89 is substantially circular in shape and has a thin base 90 and a substantially centrally positioned male taper 91, as seen in FIG. 15b. FIG. 15c shows a 20 stem-extension 85, comprising a cavity 86 and a stem 87 with a tapered end 88.

FIGS. 16a and 16b show a shoulder prosthesis assembly 110 using the components as described in connection with FIGS. 15a to 15c. In a first assembly step, the ball-head 81 is inserted into the cavity 86 of the stem-extension 85. In a next step, the base portion 89 is connected to the ball-head 81. Finally, the humeral stem 10 is connected to the stem25 extension 85.

Figure 17:
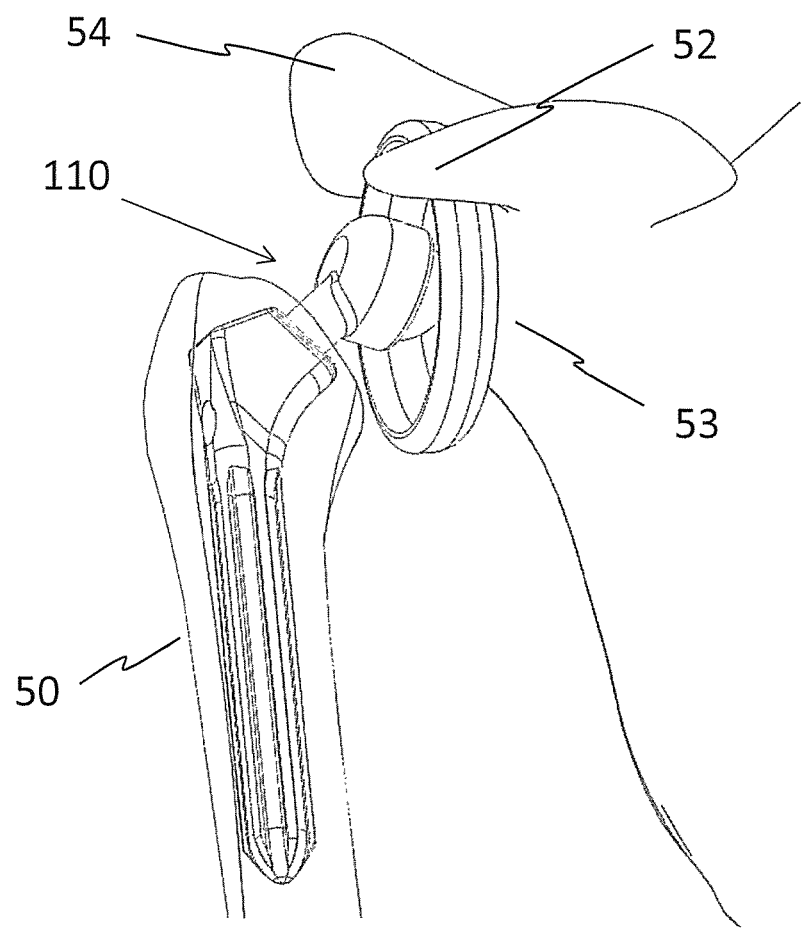
FIG. 17 a representation of implanted shoulder prosthesis as shown in FIGS. 16a, 16b.

The implanted shoulder prosthesis assembly 110 according to FIGS. 16a and 16b is shown in FIG. 17. The humeral stem 10 is inserted into the humeral bone 50. The base portion 13 engages with the glenoid 53, acromion 54 and the coracoid 52.

Figure 18A:
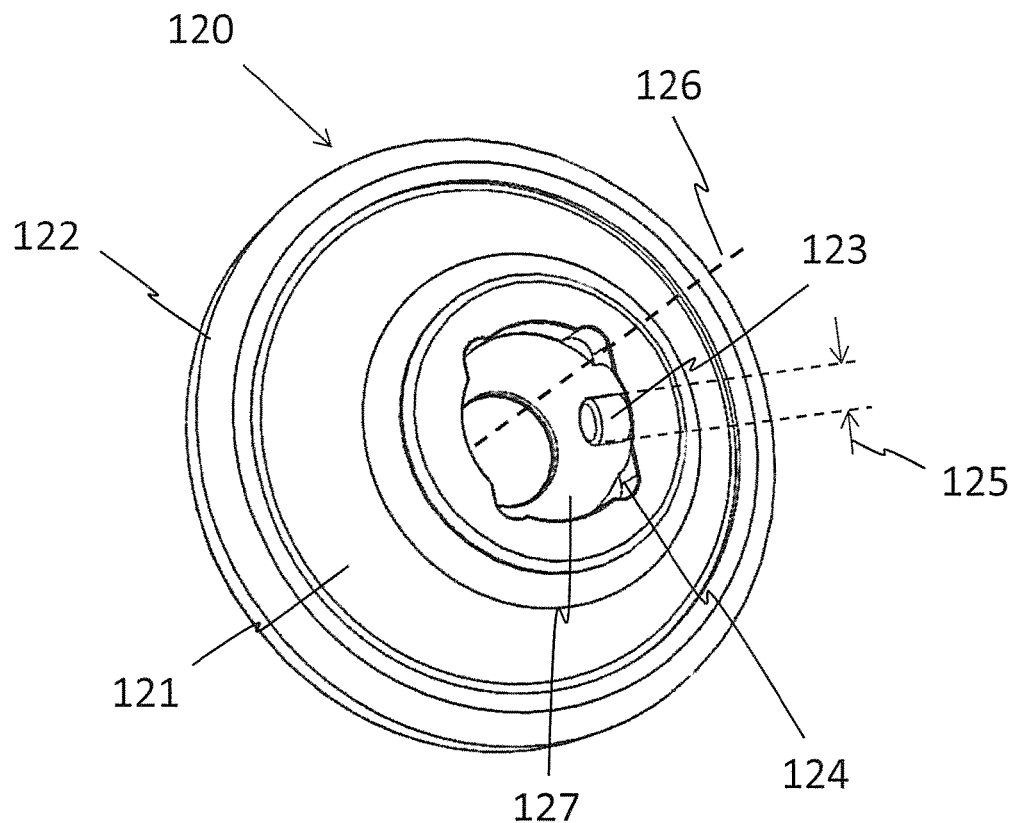
FIGS. 18a, 18b an alternative embodiment of the ball-and-socket coupling.
Figure 18B:
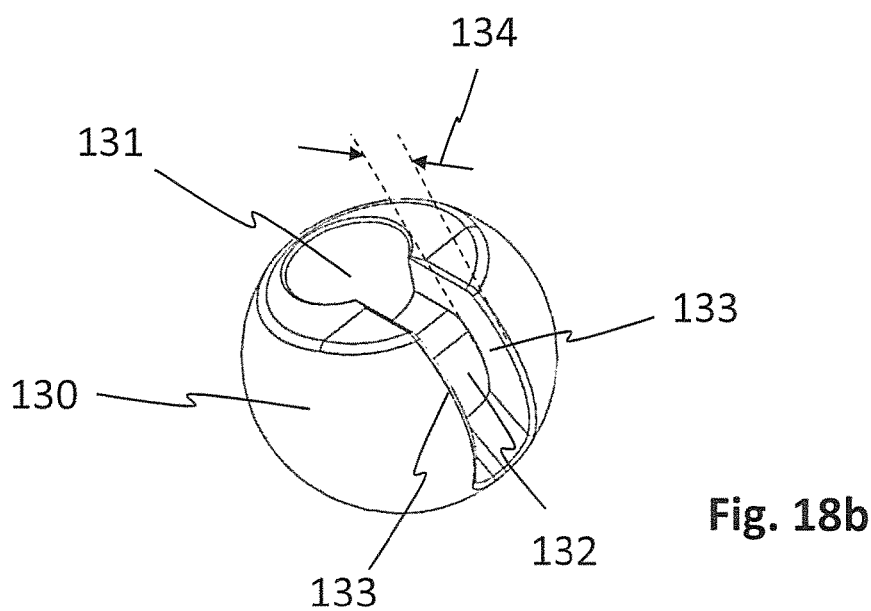

FIGS. 18a and 18b show an alternative embodiment for the ball-in-socket joint coupling. FIG. 18a represents the substantially circular base portion 120. The base portion 120 comprises an inner inlay 121 and an outer metal base 122. The inner inlay 121 is rotatably coupled to the outer metal base 122 such as to be rotatable around a fourth axis of rotation 126, which is substantially perpendicular to outer metal base 122. The inner inlay 121 comprises a spherically shaped cavity 127 with an intersecting pocket 124. The spherical articulation cavity 127 is positioned offset from the centre of the base portion 120. The inner inlay 121 further comprises a nose 123. The nose 123 is preferably circular or hemispherical with a diameter 125 being larger than 2 mm but smaller than 15 mm. The nose 123 is directed towards the centre of the spherical cavity 127, wherein the central axis of the nose 123 intersects with the centre of spherical cavity 127.

FIG. 18b depicts the ball-head 130. The ball-head 130 comprises a connection interface 131, preferably in the form of a female taper. Additionally, the ball-head 130 comprises a groove 132 along a circular largest circumference. The groove 132 has side walls 133, wherein a distance between the side-walls 133 is equal to or larger as diameter 125. The depth 134 of the groove 132 is equal or larger than the length of the nose 123.

Figure 19D:
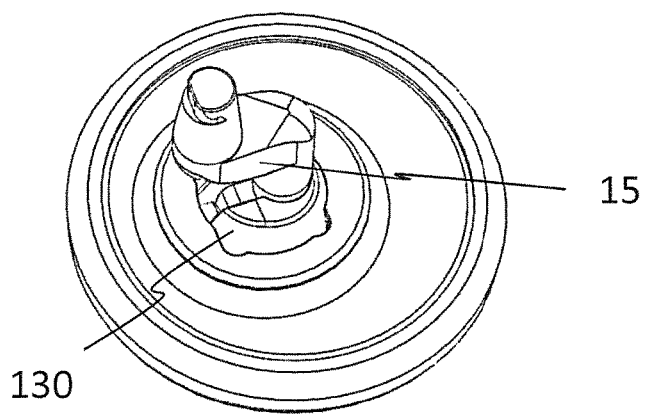
Figure 19E:
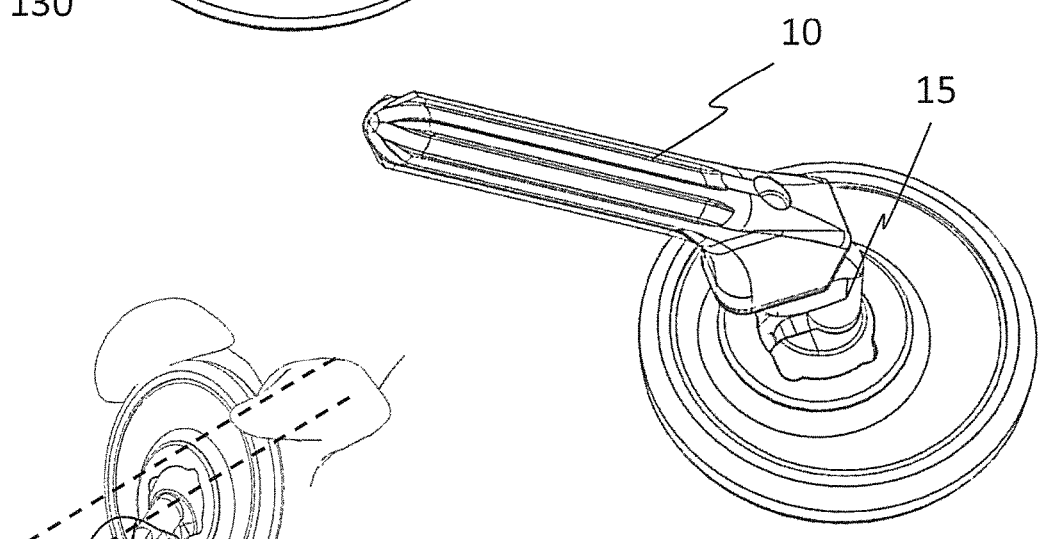

FIGS. 19a to 19c show the interplay between the described elements according to FIGS. 18a and 18b. The ball-head 130 is assembled into the spherical articulation cavity 127 of the inner inlay 121 by orienting faces of the ball-head 131 such that they are aligned with the sidewalls of pocket 124. In this way, the nose 123 may be inserted into groove 132, as seen in FIG. 19a. When a first end-position, shown in FIG. 19b, is reached, the ball-head 131 is turned by approximately 90° into a second end-position, as shown in FIG. 19c. In this second end-position, the connection interface 131 is accessible through pocket 124. This allows the introduction of the adaptor 15 into the connection interface 131, as may be seen in FIG. 19d. Finally, the humeral stem 10 is connected with the adaptor 15, as shown in FIG. 19e.

Figure 19F:
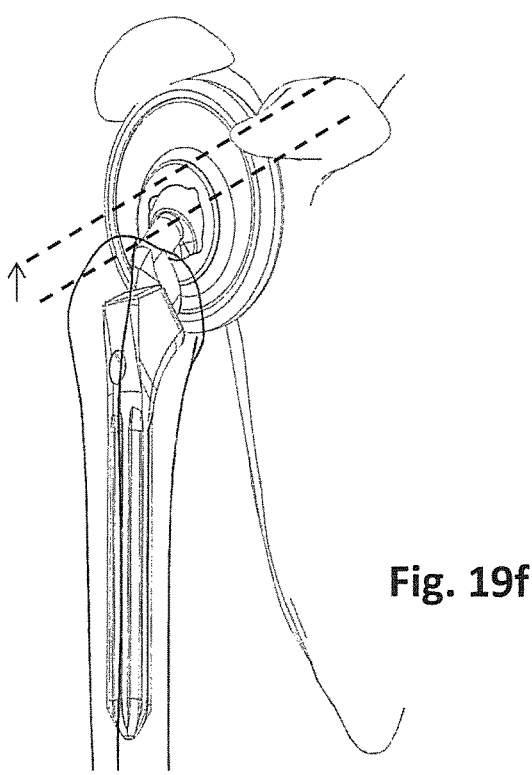

The nose 123 eliminates one rotational degree of freedom of the ball-and-socket connection. The ball-head 130 can only rotate along groove 132 and around the central axis of the nose 123. The rotational degree of freedom substantially perpendicular to the base portion 120 is blocked by the interaction of the nose 123 and the side-walls 133 of the groove 132. This missing rotational degree of freedom is compensated by the rotatable coupling between the outer metal base 122 and the inner inlay 121. As the fourth axis of rotation 126 does not intersect with the remaining two axes of rotation of the ball-head 130, the rotation of the ball head around said axis is in a more distal position in comparison to the embodiment of the shoulder prosthesis assembly 100 as shown for FIGS. 1 to 3. This distal shifting of the axis of rotation is shown in FIG. 19f.

Figure 20:
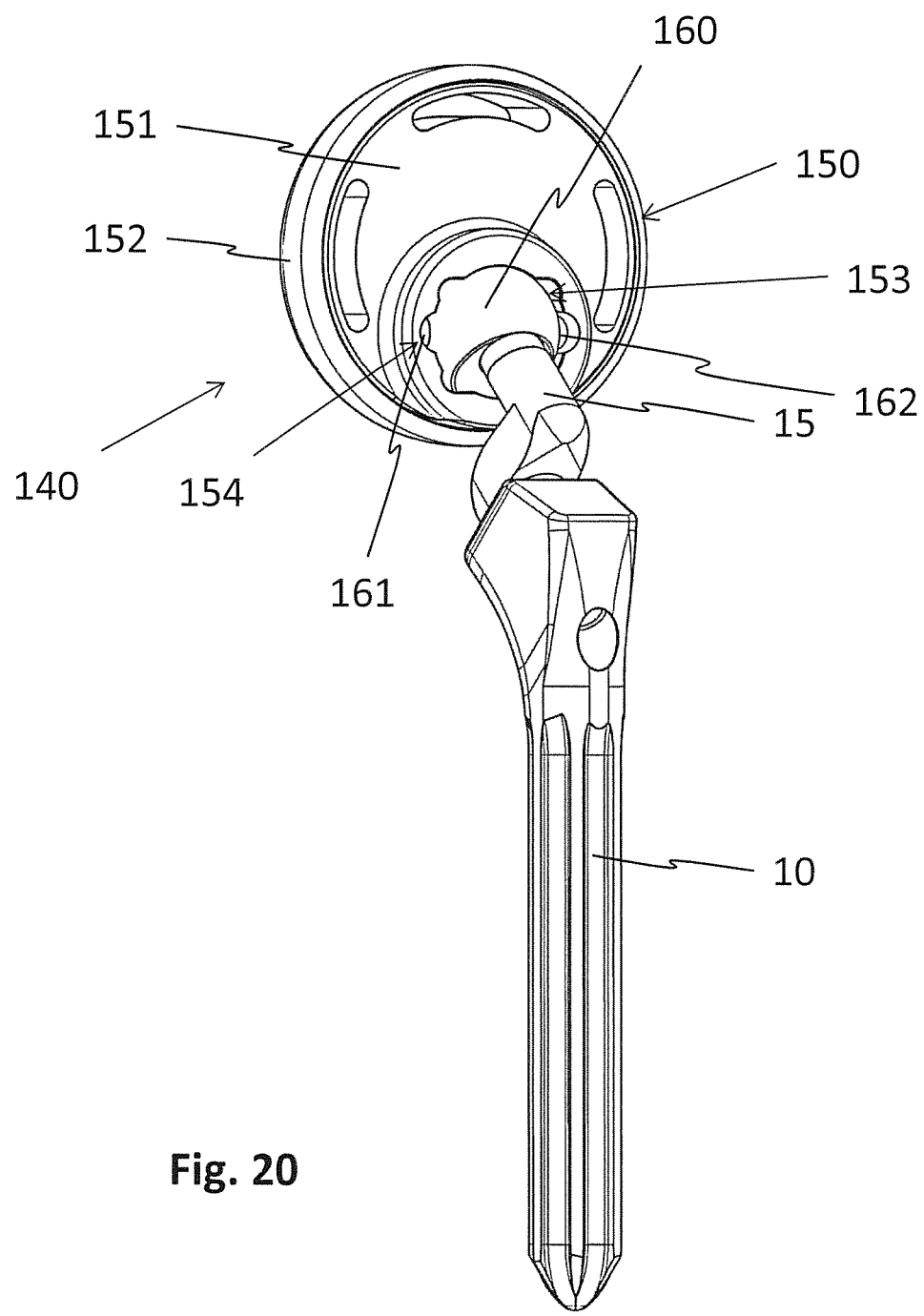
FIG. 20 a further embodiment of a shoulder prosthesis assembly according to the present invention.

FIG. 20 shows a further embodiment of a shoulder prosthesis assembly 140 according to the present invention. The base portion 150 comprises an inner inlay 151 which is rotatably coupled to an outer metal base 152. Further, a ball-head 160 is movingly arranged within a socket 153 of the inner inlay 151. The ball-head 160 and the socket 153 form a ball-and-socket connection. An adaptor 15 is connected to the ball-head 160, said adaptor 15 being further attached to a humeral stem 10.

The socket 153 includes a channel 154 into which two protuberances 161, 162 provided on said ball-head 160 are engaged. The channel 154 as well as the protuberances 161, 162 have a matching hemispherical shape. Without provision of the channel 154 and the protuberances 161, 162 the ball-head 160 would be able to rotate freely around three axes of rotation within the socket. However, the engagement of the two protuberances 161, 162 into the channel 154 restricts rotational movement of the ball-head 160 around one axis, as the two protuberances 161, 162 are form-fittingly engaged within the channel 154. This results in a movement restriction of the ball-and-socket connection in one degree of freedom. In the shown embodiment, the channel 154 has the same shape and width as the two protuberances 161, 162, hence any movement around the blocked rotation axis are prevented. Alternatively, the channel 154 may have a width which is slightly larger than the width of the two protuberances 161, 162. With such an alternative embodiment, the ball-head 160 would be able to carry out small movements around the blocked axis, hence enabling a limited "wobbling" of the ball-head 160 within the socket 153.

Rotational movement of the ball-head 160 around the two other axes of rotation is enabled by a sliding motion of the two protuberances 161, 162 within the channel 154 and rotational movement of the two protuberances 161, 162 within the channel 154.

Figure 21A:
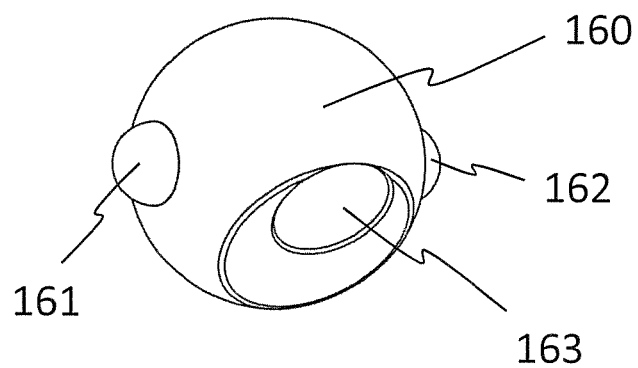
FIGS. 21a, 21b a detailed view of the base portion and the ball head of the shoulder prosthesis assembly according to FIG. 20.

FIG. 21*a* shows a detailed view of the base portion 150 of the shoulder prosthesis assembly 140 according to FIG. 20. The shape of the two protuberances 161, 162 as well as of the ball-head 160 may be clearly recognized in this figure. As may be seen, the ball-head 160 is in the shape of a dome, i.e. of a sphere which is cut by a plane, while the two protuberances 161, 162 are in the form of hemispheres.

Figure 21B:
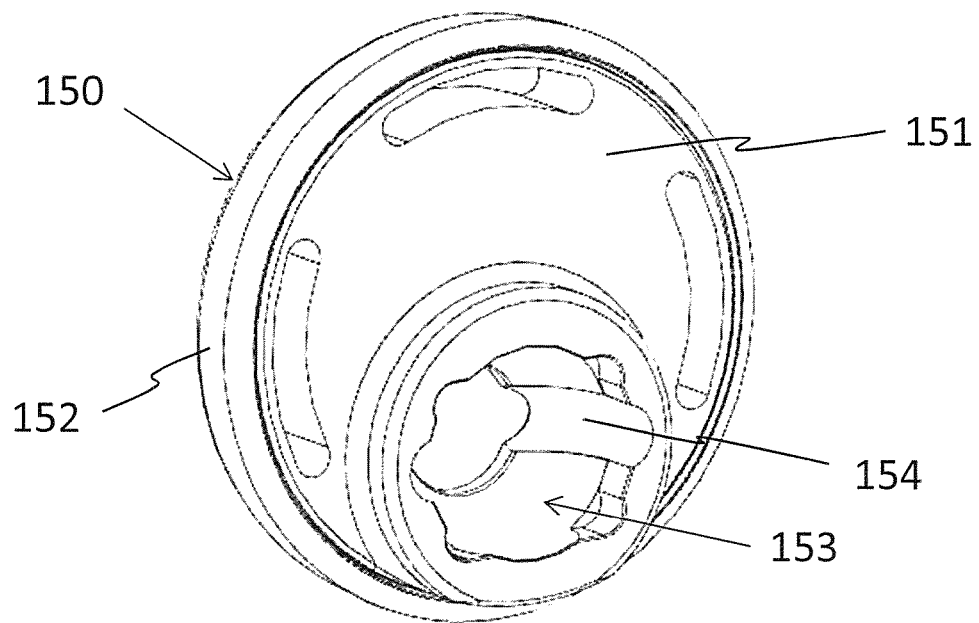

FIG. 21*b* shows a detailed view of the ball-head 160 of the shoulder prosthesis assembly 140 according to FIG. 20. As may be seen, the channel 154 has a hemispherical shape and is arranged on the socket 153 along a great circle. The channel 154 thereby spans the socket 153 from edge to edge.

Figure 22:
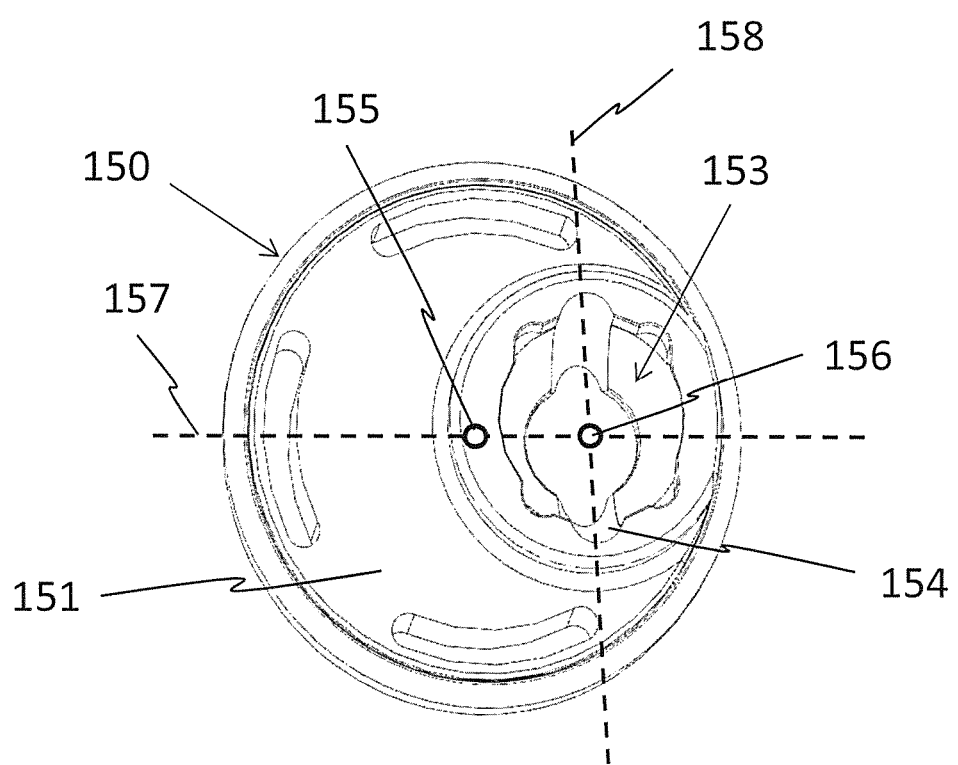
FIG. 22 the orientation of the channel relative to the inlay according to the embodiment as shown in FIGS. 20 and 21.

FIG. 22 depicts the orientation of the channel 154, which is represented by the channel axis 158, relative to the inner inlay 151. In the embodiment shown, the channel 154 is oriented perpendicular to an imaginary line 157 which connects the axis of rotation 156 of the inner inlay 157 and the centre of rotation 156 of the ball-and-socket connection. In other words the angle between the imaginary line 157 and the channel axis 158 is 90°.

In a further embodiment (not shown) the channel axis 158 is parallel to the imaginary line 157. In other words the angle between the imaginary line 157 and the channel axis 158 is 0°.

As a person having skill in the art recognizes, the orientation of the groove 132 according to the embodiment shown in FIGS. 18 and 19 may likewise be oriented parallel or perpendicular so said imaginary line 157.

We claim:

1. A shoulder prosthesis assembly comprising a humeral stem, a first articulating coupling means, a base portion of a substantially disc shaped geometry including a second articulating coupling means, the first articulating coupling means and the second articulating coupling means connecting the stem to the base portion, the base portion being movably coupled to the stem by means of an at least three degrees of freedom coupling, wherein the base portion comprises an inner inlay and is movably coupled to the stem by means of the inlay comprising a ball-and-socket coupling with one blocked rotational degree of freedom, wherein the inlay comprises an axis of rotation and is rotatably coupled to a base of the base portion, wherein a ball head of the ball-and-socket coupling is locked in a socket of the ball-and-socket coupling by a form-fit connection, and wherein the ball-and-socket coupling is positioned offset from the axis of rotation of the inlay.

2. The shoulder prosthesis assembly of claim 1, wherein an outer rim of the base portion is in the form of a polygon or is irregularly shaped.

3. The shoulder prosthesis assembly of claim 1, wherein the at least three degrees of freedom coupling has three rotational degrees of freedom.

4. The shoulder prosthesis assembly of claim 3, wherein the base portion is movably coupled to the stem by means of said ball-and-socket connection.

5. The shoulder prosthesis assembly of claim 3, wherein the base portion is movably coupled to the stem portion by means of a gimbal-mount coupling.

6. The shoulder prosthesis assembly according to any one of the preceding claims, wherein the ratio between the circumference of the disc shaped base portion and the peripheral thickness of the disc shaped base portion is at least 18:1.

7. The shoulder prosthesis assembly of claim 3 comprising a substantially Z-shaped adaptor arranged between said ball-head and said humeral stem.

8. The shoulder prosthesis assembly of claim 7, wherein the adaptor comprises two tapered ends, wherein the central axes of the tapered ends are oriented either offset in one direction and parallel to each other or offset in one direction and under an acute angle to each other.

9. The shoulder prosthesis assembly according to claim 1, wherein said second articulating coupling means of said ball-and-socket connection comprises a spherical articulation cavity or a socket, said spherical articulation cavity including a groove and said socket including a channel, wherein said groove or said channel is oriented parallel or perpendicular to an imaginary line connecting the axis of rotation of said inlay and a rotational centre of said ball-and-socket coupling.

10. The shoulder prosthesis assembly of claim 1, wherein said ball-and-socket connection comprises a ball-head in the form of a spherical cap, a connection interface for connecting said humeral stem with said ball-head being arranged on the base of said ball-head, wherein said connection interface is located offset of the centre of the base of the ball-head.

11. The shoulder prosthesis assembly of claim 10, wherein said ball-head is in the form of a spherical segment and a socket of said ball-and-socket coupling has an opening which is smaller than a largest diameter of said ball-head but larger than a distance between faces of said ball-head.

12. The shoulder prosthesis assembly of claim 1, wherein the base portion is dimensioned such that a distance between the centre of rotation of said at least three degrees of freedom coupling and a base area of said base portion is less than 15 mm.

13. The shoulder prosthesis assembly according to claim 1, wherein at least one portion of a rim of said base portion comprises an increased thickness.

14. The shoulder prosthesis assembly according to claim 1, comprising a base portion with a proximal face and an outer rim with a circumference, wherein the proximal face has a concave, convex or conical surface with a height or a depth, wherein the circumference to height ratio or circumference to depth ratio is at least 15:1, preferably larger than 20:1.

\* \* \* \* \*